US012648926B2

(12) United States Patent
Coe

(10) Patent No.: US 12,648,926 B2
(45) Date of Patent: Jun. 9, 2026

(54) DIETARY SUPPLEMENT COMPRISING ALDEHYDE FUNCTIONAL MONOTERPENOIDS

(71) Applicant: William B. Coe, Wrightwood, CA (US)

(72) Inventor: William B. Coe, Wrightwood, CA (US)

( * ) Notice: Subject to any disclaimer, the term of this patent is extended or adjusted under 35 U.S.C. 154(b) by 833 days.

(21) Appl. No.: 17/906,186

(22) PCT Filed: Mar. 16, 2021

(86) PCT No.: PCT/US2021/022610
§ 371 (c)(1),
(2) Date: Sep. 12, 2022

(87) PCT Pub. No.: WO2021/188575
PCT Pub. Date: Sep. 23, 2021

(65) Prior Publication Data

US 2023/0116276 A1 Apr. 13, 2023

Related U.S. Application Data

(63) Continuation-in-part of application No. 16/882,130, filed on May 22, 2020, now Pat. No. 10,993,958.

(60) Provisional application No. 63/038,672, filed on Jun. 12, 2020, provisional application No. 63/036,610, filed on Jun. 9, 2020, provisional application No. 63/035,581, filed on Jun. 5, 2020, provisional application No. 63/000,384, filed on Mar. 26, 2020, provisional application No. 62/993,304, filed on Mar. 23, 2020, provisional application No. 62/990,223, filed on Mar. 16, 2020.

(51) Int. Cl.

| | |
|---|---|
| ***A61K 31/352*** | (2006.01) |
| ***A61K 9/00*** | (2006.01) |
| ***A61K 31/11*** | (2006.01) |
| ***A61K 31/7084*** | (2006.01) |
| ***A61K 33/30*** | (2006.01) |
| ***A61K 36/48*** | (2006.01) |
| ***A61K 47/10*** | (2017.01) |
| ***A61P 9/00*** | (2006.01) |
| ***A61P 25/24*** | (2006.01) |

(52) U.S. Cl.
CPC ............ *A61K 31/352* (2013.01); *A61K 9/006* (2013.01); *A61K 31/11* (2013.01); *A61K 31/7084* (2013.01); *A61K 33/30* (2013.01); *A61K 36/48* (2013.01); *A61K 47/10* (2013.01); *A61P 9/00* (2018.01); *A61P 25/24* (2018.01)

(58) Field of Classification Search
CPC ...... A61K 31/352; A61K 9/006; A61K 31/11; A61K 31/7084; A61K 33/30; A61K 36/48; A61K 47/10; A61P 9/00; A61P 25/24
See application file for complete search history.

(56) References Cited

U.S. PATENT DOCUMENTS

| | | | | |
|---|---|---|---|---|
| 8,003,688 | B2 | 8/2011 | Berg | |
| 10,993,958 | B1 | 5/2021 | Coe | |
| 11,612,616 | B2 | 3/2023 | Coe | |
| 2005/0245467 | A1 | 11/2005 | Berg | |
| 2006/0276393 | A1 * | 12/2006 | Milburn | A61P 11/00 514/183 |
| 2007/0116779 | A1 | 5/2007 | Mazzio et al. | |

FOREIGN PATENT DOCUMENTS

| | | |
|---|---|---|
| WO | WO 10/056413 | 5/2010 |

OTHER PUBLICATIONS

Prema et al., "Fenugreek Seed Powder Nullified Aluminium Chloride Induced Memory Loss, Biochemical Changes, Aβ Burden and Apoptosis via Regulating Akt/GSK3β Signaling Pathway," PLoS One. Nov. 28, 2016;11(11):e0165955. (Year: 2016).*
Venkata et al., "A small plant with big benefits: Fenugreek (Trigonella foenum-graecum Linn.) for disease prevention and health promotion," Mo. Nutr. Food Res. 61, 6, 2017. (Year: 2017).*
Kodomuri et al., " Fenugreek seed extract ameliorates cognitive deficits in streptozotocin-induced diabetic rats," J Basic Clin Physiol Pharmacol. Jul. 20, 2019;30(4). (Year: 2019).*
Maher et al., "Fisetin Lowers Methylglyoxal Dependent Protein Glycation and Limits the Complications of Diabetes," PLOS One (Jun. 2011), vol. 6, Issue 6. (Year: 2011).*
Currais et al., "Fisetin Reduces the Impact of Aging on Behavior and Physiology in the Rapidly Aging SAMP8 Mouse," J Gerontol A Biol Sci Med Sci, 2018, vol. 73, No. 3, 299-307. (Year: 2018).*
Byun et al., 2016, Effects of air pollution and blood mitochondrial DNA methylation on markers of heart rate variability, Journal of the Americal Heart Association, DOI: 10/1161/JAHA. 116.003218, 10 pp.
Ferrari et al., 2019, Particulate matter exposure shapes DNA methylation through the lifespan. Clin Epigenet 11:129, https://doi.org/10.1186/s13148-019-0726-x, 14 pp.
Ghosh et al., 2015, Fenugreek (trigonella foenum-graecum L.) and its necessity [review [paper], Fire Journal of Engineering and Technology, 1(1):60-67.
Snider et al., 2016, Variation in global chemical composition of $PM_{2.5}$: emerging results from Spartan, Atmos. Chem. Phys., 16:9629-9653.
Suschke et al., 2007. Antibacterial and cytotoxic activity of *Nepeta cataria* L., N. cataria var. citriodora (beck.) Balb. And *Melissa officinalis* L. essential oils, Natural Product Communications, 2(12): 1277-1286.
International Search Report and Written Opinion dated Jul. 2, 2021 in application No. PCT/US2021/022610.

* cited by examiner

*Primary Examiner* — Jared Barsky
(74) *Attorney, Agent, or Firm* — Knobbe, Martens, Olson & Bear, LLP

(57) ABSTRACT

Compositions comprising aldehyde functional monoterpenoids in combination with 3,3',4',7-tetrahydroxyflavone, zinc, and a 5-beta-D-Ribofuranosylpicolineamide adenine-dinucleotide molecule are provided for treating viral infections, e.g., coronavirus infections such as COVID-19, and/or enhancing mood.

4 Claims, 5 Drawing Sheets

DIETARY SUPPLEMENT COMPRISING ALDEHYDE FUNCTIONAL MONOTERPENOIDS

INCORPORATION BY REFERENCE TO RELATED APPLICATIONS

Any and all priority claims identified in the Application Data Sheet, or any correction thereto, are hereby incorporated by reference under 37 CFR 1.57. This application is the U.S. National Phase of International Application No. PCT/US2021/022610, filed Mar. 16, 2021, titled "DIETARY SUPPLEMENT COMPRISING ALDEHYDE FUNCTIONAL MONOTERPENOIDS," which claims the benefit of U.S. Provisional Application No. 62/990,223, filed Mar. 16, 2020; U.S. Provisional Application No. 62/993,304, filed Mar. 23, 2020; U.S. Provisional Application No. 63/000,384, filed Mar. 26, 2020; U.S. application Ser. No. 16/882,130, filed May 22, 2020; U.S. Provisional Application No. 63/035,581, filed Jun. 5, 2020; U.S. Provisional Application No. 63/036,610, filed Jun. 9, 2020; and U.S. Provisional Application No. 63/038,672, filed Jun. 12, 2020. Each of the aforementioned applications is incorporated by reference herein in its entirety, and each is hereby expressly made a part of this specification.

FIELD

Compositions comprising aldehyde functional monoterpenoids in combination with 3,3',4',7-tetrahydroxyflavone, zinc, and a 5-beta-D-Ribofuranosylpicolineamide adenine-dinucleotide molecule are provided for treating viral infections, e.g., coronavirus infections such as COVID-19, and/or enhancing mood.

BACKGROUND

Coronaviruses are a large family of viruses that usually cause mild to moderate upper-respiratory tract illnesses, like the common cold, in people. However, three times in the 21st century coronavirus outbreaks have emerged from animal reservoirs to cause severe disease and global transmission concerns.

There are hundreds of coronaviruses, most of which circulate among animals including pigs, camels, bats and cats. Sometimes those viruses jump to humans—called a spillover event—and can cause disease. Seven coronaviruses are known to cause human disease, four of which are mild: viruses 229E, OC43, NL63 and HKU1. Three of the coronaviruses can have more serious outcomes in people, and those diseases are SARS (severe acute respiratory syndrome) which emerged in late 2002 and disappeared by 2004; MERS (Middle East respiratory syndrome), which emerged in 2012 and remains in circulation in camels; and COVID-19, which emerged in December 2019 from China and a global effort is under way to contain its spread. COVID-19 is caused by the coronavirus known as SARS-CoV-2.

When SARS emerged from China in 2002 it swept across the globe—largely through air travel—causing deadly illness. More than 8,000 people fell ill and 774 died, numbers COVID-19 surpassed within two months. SARS drew the collective focus of researchers throughout the world. The disease disappeared in 2004, likely due to isolation and quarantine containment measures, and no cases of SARS have been reported since. In 2012, a new coronavirus emerged in the Middle East causing an illness similar to SARS. Again, researchers across the globe initiated studies to understand MERS-CoV and how to stop it. Research efforts from those two outbreaks—including development of a DNA vaccine candidate for SARS by NIAID's Vaccine Research Center—have prepared scientists to quickly assess the severity and transmission potential of SARS-CoV-2, and to develop countermeasures.

When MERS emerged in 2012 and COVID-19 was identified in 2020, scientists mobilized quickly to study the viruses, efforts which continue today. Key areas of investigation include basic research on their origins, how they cause disease, and developing animal study models, new treatments, and vaccines.

SUMMARY

Treatments that are effective against viral infections, including coronavirus infections such as COVID-19, are desirable. Accordingly, antiviral and/or antiangiogenic compositions targeting viral infection are provided. Methods are provided for administering the compositions. The compositions are also effective in treating respiratory complications surrounding lung conditions such as lung based, small cell carcinoma, mesothelioma, and chronic obstructive pulmonary disease (COPD).

Accordingly, in a generally applicable first aspect (i.e., independently combinable with any of the aspects or embodiments identified herein), a method of treatment of an infection of the lung, comprising: administering, to a patient in need thereof, an effective amount of an aldehyde functional monoterpenoid (e.g., optionally three aldehyde functional monoterpenoids comprising neral, geranial, and citronellal), an effective amount of 3,3',4',7-tetrahydroxyflavone, optionally an effective amount of zinc in ionic form, and optionally an effective amount of a 5-beta-D-Ribofuranosylpicolineamide adenine-dinucleotide molecule.

In an embodiment of the first aspect (i.e., independently combinable with any of the aspects or embodiments identified herein), the method of treatment of an infection of the lung comprises: administering, to a patient in need thereof, an effective amount of three aldehyde functional monoterpenoids comprising neral, geranial, and citronellal, and an effective amount of 3,3',4',7-tetrahydroxyflavone.

In an embodiment of the first aspect (i.e., independently combinable with any of the aspects or embodiments identified herein), the 3,3',4',7-tetrahydroxyflavone is provided in a form of a complex with at least one of the aldehyde functional monoterpenoids via grafting at a carbonyl site of the least one of the aldehyde functional monoterpenoids.

In an embodiment of the first aspect (i.e., independently combinable with any of the aspects or embodiments identified herein), the complex is provided as a suspension of clusters having a mean longest dimension of 10 nm to 50 nm.

In an embodiment of the first aspect (i.e., independently combinable with any of the aspects or embodiments identified herein), the suspension is an emulsion in a mixture of water and vegetable glycerin.

In an embodiment of the first aspect (i.e., independently combinable with any of the aspects or embodiments identified herein), at least one of the aldehyde functional monoterpenoids is an ionophore for the zinc in ionic form.

In an embodiment of the first aspect (i.e., independently combinable with any of the aspects or embodiments identified herein), the zinc in ionic form is provided as zinc gluconate.

In an embodiment of the first aspect (i.e., independently combinable with any of the aspects or embodiments identified herein), the suspension comprises 0.001%-20% by weight (e.g., 1%-20% by weight, e.g., 5-15% by weight) by weight of neral, 0.001%-20% by weight (e.g., 1%-20% by weight, e.g., 5-15% by weight) by weight of geranial, 0.001%-20% by weight (e.g., 1%-20% by weight, e.g., 5-15% by weight) by weight of citronellal, 0.001%-20% by weight (e.g., 1%-20% by weight, e.g., 5-15% by weight) by weight of ionic zinc, 0.001%-20% by weight (e.g., 1%-20% by weight, e.g., 5-15% by weight) of 3,3',4',7-tetrahydroxyflavone, and 0.001%-20% by weight (e.g., 1%-20% by weight, e.g., 5-15% by weight) by weight of the 5-beta-D-Ribofuranosylpicolineamide adenine-dinucleotide molecule.

In an embodiment of the first aspect (i.e., independently combinable with any of the aspects or embodiments identified herein), the suspension comprises 0.001%-10% by weight of neral, 0.001%-10% by weight of geranial, 0.001%-10% by weight of citronellal, 0.001%-10% by weight of ionic zinc, 0.001%-10% by weight of 3,3',4',7-tetrahydroxyflavone, and 0.001%-10% by weight of the 5-beta-D-Ribofuranosylpicolineamide adenine-dinucleotide molecule.

In an embodiment of the first aspect (i.e., independently combinable with any of the aspects or embodiments identified herein), the suspension is adapted to be delivered to the patient by inhalation in a form of a vapor, a mist, or an aerosol.

In an embodiment of the first aspect (i.e., independently combinable with any of the aspects or embodiments identified herein), the suspension is delivered continuously until relief from symptoms of the infection of the lung is observed.

In an embodiment of the first aspect (i.e., independently combinable with any of the aspects or embodiments identified herein), the suspension is delivered for 2-8 hours until relief from symptoms of the infection of the lung is observed.

In an embodiment of the first aspect (i.e., independently combinable with any of the aspects or embodiments identified herein), the suspension is delivered for 2-8 hours once every 2-3 days until relief from symptoms of the infection of the lung is observed.

In an embodiment of the first aspect (i.e., independently combinable with any of the aspects or embodiments identified herein), the suspension is delivered for 1-3 weeks or until relief from symptoms of the infection of the lung is observed.

In an embodiment of the first aspect (i.e., independently combinable with any of the aspects or embodiments identified herein), the suspension is readministered if the symptoms of the infection of the lung reoccur.

In an embodiment of the first aspect (i.e., independently combinable with any of the aspects or embodiments identified herein), the infection of the lung is a viral infection.

In an embodiment of the first aspect (i.e., independently combinable with any of the aspects or embodiments identified herein), the viral infection is a coronavirus infection.

In an embodiment of the first aspect (i.e., independently combinable with any of the aspects or embodiments identified herein), the coronavirus infection is COVID-19.

In a second aspect, a pharmaceutical composition is provided comprising three aldehyde functional monoterpenoids comprising neral, geranial, and citronellal, zinc in ionic form, 3,3',4',7-tetrahydroxyflavone, and a 5-beta-D-Ribofuranosylpicolineamide adenine-dinucleotide molecule.

In a third aspect, a method of treatment of an infection of the lung is provided, comprising: administering, to a patient in need thereof, by inhalation in a form of a vapor, a mist, or an aerosol, a suspension of an effective amount of three aldehyde functional monoterpenoids comprising neral, geranial, and citronellal, an effective amount of zinc in ionic form, an effective amount of 3,3',4',7-tetrahydroxyflavone, and an effective amount of a 5-beta-D-Ribofuranosylpicolineamide adenine-dinucleotide molecule.

In an embodiment of the third aspect (i.e., independently combinable with any of the aspects or embodiments identified herein), the 3,3',4',7-tetrahydroxyflavone is provided in a form of a complex with at least one of the aldehyde functional monoterpenoids via grafting at a carbonyl site of the least one of the aldehyde functional monoterpenoids.

In an embodiment of the third aspect (i.e., independently combinable with any of the aspects or embodiments identified herein), the complex is provided as a suspension of clusters having a mean longest dimension of 10 nm to 50 nm.

In an embodiment of the third aspect (i.e., independently combinable with any of the aspects or embodiments identified herein), the suspension is an emulsion in a mixture of water and vegetable glycerin.

In an embodiment of the third aspect (i.e., independently combinable with any of the aspects or embodiments identified herein), at least one of the aldehyde functional monoterpenoids is an ionophore for the zinc in ionic form.

In an embodiment of the third aspect (i.e., independently combinable with any of the aspects or embodiments identified herein), the zinc in ionic form is provided as zinc gluconate.

In an embodiment of the third aspect (i.e., independently combinable with any of the aspects or embodiments identified herein), the suspension comprises 0.001%-20% by weight of neral, 0.001%-20% by weight of geranial, 0.001%-20% by weight of citronellal, 0.001%-20% by weight of 3,3',4',7-tetrahydroxyflavone, 0.001%-20% by weight of zinc, and 0.001%-20% by weight of a 5-beta-D-Ribofuranosylpicolineamide adenine-dinucleotide molecule.

In an embodiment of the third aspect (i.e., independently combinable with any of the aspects or embodiments identified herein), the suspension is adapted to be delivered to the patient by inhalation in a form of a vapor, a mist, or an aerosol.

In an embodiment of the third aspect (i.e., independently combinable with any of the aspects or embodiments identified herein), the suspension is delivered for 2-8 hours per day until relief from symptoms of the infection of the lung is observed.

In an embodiment of the third aspect (i.e., independently combinable with any of the aspects or embodiments identified herein), the suspension is readministered if the symptoms of the infection of the lung reoccur.

In an embodiment of the third aspect (i.e., independently combinable with any of the aspects or embodiments identified herein), the suspension is delivered for 2-8 hours once every 2-3 days until relief from symptoms of the infection of the lung is observed.

In an embodiment of the third aspect (i.e., independently combinable with any of the aspects or embodiments identified herein), the suspension is delivered continuously until relief from symptoms of the infection of the lung is observed.

In an embodiment of the third aspect (i.e., independently combinable with any of the aspects or embodiments identified herein), the infection of the lung is a viral infection.

In an embodiment of the third aspect (i.e., independently combinable with any of the aspects or embodiments identified herein), the viral infection is a coronavirus infection.

In an embodiment of the third aspect (i.e., independently combinable with any of the aspects or embodiments identified herein), the coronavirus infection is COVID-19.

In a fourth aspect, a composition is provided comprising: 1.8% by weight fisetin; 3.6% by weight glycerin; 12.6% by weight of a combination of fenugreek essential oil:glycerin:water in a ratio by weight of 20:20:60; 12.6% by weight of a combination of lemon balm essential oil:glycerin:water in a ratio by weight of 20:20:60; 1.0% by weight of a tincture of curcumin:fruit alcohol-ethanol:water in a ratio by weight of 10:10:80); 1.0% by weight of a combination of anise star essential oil: glycerin: water in a ratio by weight of 20:20:60; and 67.4% by weight water.

In a fifth aspect, a method of prophylaxis or treatment of a lung infection is provided, comprising administering the composition of the fourth aspect to a patient in need thereof by inhalation in a form of a vapor, a mist, or an aerosol.

In a sixth aspect, a method of prophylaxis or treatment of COVID-19 is provided, comprising administering the composition of the fourth aspect to a patient in need thereof by inhalation in a form of a vapor, a mist, or an aerosol.

In a seventh aspect, a method of prophylaxis or treatment of cough is provided, comprising administering the composition of the fourth aspect to a patient in need thereof by inhalation in a form of a vapor, a mist, or an aerosol.

In an eighth aspect, a method of prophylaxis or treatment of sinus or lung congestion is provided, comprising administering the composition of the fourth aspect to a patient in need thereof by inhalation in a form of a vapor, a mist, or an aerosol.

In a ninth aspect, a method of prophylaxis or treatment of chest pain is provided, comprising administering the composition of the fourth aspect to a patient in need thereof by inhalation in a form of a vapor, a mist, or an aerosol.

In a tenth aspect, a method of prophylaxis or treatment of COPD is provided, comprising administering the composition of the fourth aspect to a patient in need thereof by inhalation in a form of a vapor, a mist, or an aerosol.

In an eleventh aspect, a composition is provided comprising: 60.65% by weight of fenugreek essential oil; 9.10% by weight glycerin; 30.25% by weight fisetin (dissolved or suspended to a <50 nm paste).

In an embodiment of the eleventh aspect (i.e., independently combinable with any of the aspects or embodiments identified herein), the composition is adapted for sublingual administration.

In an embodiment of the eleventh aspect (i.e., independently combinable with any of the aspects or embodiments identified herein), the composition is adapted for elevating mood.

In an embodiment of the eleventh aspect (i.e., independently combinable with any of the aspects or embodiments identified herein), the composition is adapted for alleviating symptoms associated with Alzheimer's disease.

In an embodiment of the eleventh aspect (i.e., independently combinable with any of the aspects or embodiments identified herein), the composition is adapted for alleviating symptoms associated with dementia.

In an embodiment of the eleventh aspect (i.e., independently combinable with any of the aspects or embodiments identified herein), the composition is adapted for alleviating symptoms associated with cardiovascular disease.

In a twelfth aspect, a method is provided of treating or alleviating symptoms associated with Alzheimer's disease, comprising: administering, to a patient in need thereof, a composition comprising an effective amount of 3,3',4',7-tetrahydroxyflavone.

In a thirteenth aspect, a method is provided of treating or alleviating symptoms associated with dementia, comprising: administering, to a patient in need thereof, a composition comprising an effective amount of 3,3',4',7-tetrahydroxyflavone.

In a fourteenth aspect, a method is provided of treating or alleviating symptoms associated with cardiovascular disease, comprising: administering, to a patient in need thereof, a composition comprising an effective amount of 3,3',4',7-tetrahydroxyflavone.

In an embodiment of any of the twelfth through fourteenth aspects, the composition further comprises steroidal sapinogens or steroidal saponins.

In an embodiment of any of the twelfth through fourteenth aspects, the composition further comprises an effective amount of three aldehyde functional monoterpenoids comprising neral, geranial, and citronellal.

In an embodiment of any of the twelfth through fourteenth aspects, the composition further comprises fenugreek essential oil, optionally 10 wt. % to 80 wt. % of the fenugreek essential oil.

In an embodiment of any of the twelfth through fourteenth aspects, the composition further comprises an effective amount of zinc in ionic form.

In an embodiment of any of the twelfth through fourteenth aspects, the composition further comprises an effective amount of a 5-beta-D-Ribofuranosylpicolineamide adenine-dinucleotide molecule.

In an embodiment of any of the twelfth through fourteenth aspects, the composition is in a form of a chewing gum.

In an embodiment of any of the twelfth through fourteenth aspects, the composition is in a form of a lozenge.

In an embodiment of any of the twelfth through fourteenth aspects, the composition is in a form of a sublingual dissolving tablet or paste.

In a sixteenth aspect, a pharmaceutical composition is provided, comprising:

30.25% by weight fisetin; 9.10% by weight glycerin; and 60.65% by weight of fenugreek essential oil.

In an embodiment of the sixteenth aspect, the composition is for use in elevating mood.

In an embodiment of the sixteenth aspect, the composition is for use in alleviating or treating a symptom of Alzheimer's disease.

In an embodiment of the sixteenth aspect, the composition is for use in alleviating or treating a symptom of dementia.

In an embodiment of the sixteenth aspect, the composition is for use in alleviating or treating a symptom of cardiovascular disease.

In an embodiment of the sixteenth aspect, the composition is in a form of a chewing gum.

In an embodiment of the sixteenth aspect, the composition is in a form of a lozenge.

In an embodiment of the sixteenth aspect, the composition is in a form of a sublingual dissolving tablet or paste.

Any of the features of an embodiment of aspects is applicable to all other aspects and embodiments identified herein. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other aspects or embodiments. Any aspect or embodiment of a method can be performed using a composition of another aspect or embodiment, and any aspect or embodiment of a composition can be adapted to be used in a method of another aspect or embodiment.

BRIEF DESCRIPTION OF THE DRAWINGS

Further aspects of the present disclosure will be more readily appreciated upon review of the detailed description of the various disclosed embodiments, described below, when taken in conjunction with the accompanying figures.

DETAILED DESCRIPTION OF THE EMBODIMENTS

Figure 1:
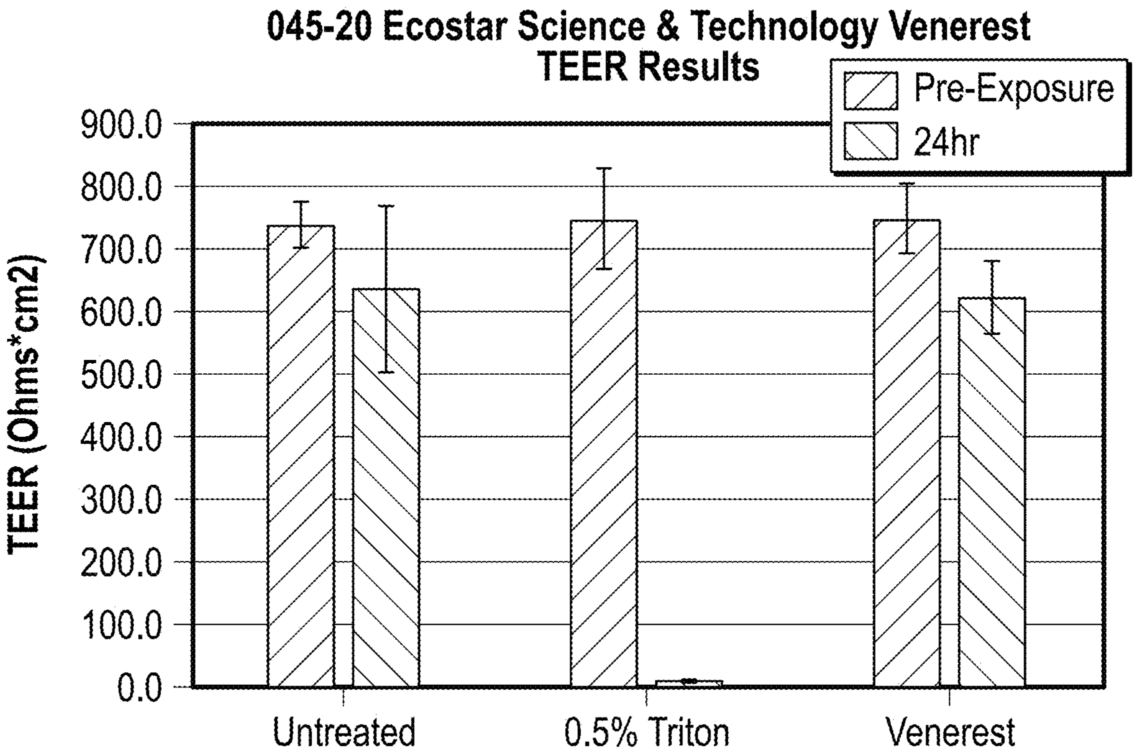
FIG. 1 provides pre-exposure and 24 hr post-exposure transepithelial electrical resistance (TEER) data for tissue that is untreated, treated with control, or treated with Venerest.

The COVID-19 pandemic is an infectious disease that a moderately functional human immune system should be able to subdue. However, many seemingly healthy adults have died or experienced severe morbidity with its effects. The virus has the world's attention that some form of physiological tipping point has been reached. Presented herein are some imposing facts that give clarity to much of the emergent, foundational health issues that have opened the door to-COVID-19 becoming a financial wrecking ball by an otherwise infectious but likely seasonal corona type pathogen.

On an average 24 hour day, in any high density population area of the planet, an individual inhales in excess of 7,000,000 individual elements of particulate matter that are smaller than 2.5 microns (PM 2.5). This is a particle size small enough to enter the blood stream, where often significant irreversible damage is done, if it is not captured and ejected at the 'front door' of the lung structure by the 'tag team' gatekeepers of: goblet cell mucus and epithelial cilia.

Outdoor—PM 2.5 Air Pollutants

Such pollutants include equivalent black carbon; crustal compounds of trace metals such as magnesium, iron, aluminum, zinc, vanadium, nickel, copper, arsenic, selenium, silver, cadmium, tin, barium, cesium, lead and mercury; water soluble ions of $NO_3^-$, $SO_4^{-2}$, $NH_4^+$, $K^+$, and Nat; trace elemental oxides; and residual matter, mostly organic. See, e.g., Atmos. Chem. Phys., 16, 9629-9653, 2016, the contents of which are hereby incorporated by reference in their entirety.

Indoor—Air Pollutants and Toxins

Biological pollutants include cockroach and bug droppings, body parts and saliva; dust mite species (used mattress may contain 100,000 to 10,000,000 mites; pet's dead skin flakes, urine, feces, saliva, hair and proteins therefrom; 200 species of mold or fungi producing glycoprotein allergens or mycotoxins. Chemical pollutants include carbon monoxide; ozone; tobacco smoke and other products of combustion (containing over 4,000 substances); volatile organic compounds from glues, art supplies, dry-cleaned clothing, cleaners, floor waxes, spot removers, air fresheners, formaldehyde, etc.; radon; pesticides (usually improperly stored); asbestos found in vermiculite in potting soil, soil conditioners, fertilizer carriers and insulation, wall board joint compound, etc.; lead absorbed from a variety of sources (occurs every day with most people); arsenic (estimated 90% of all outdoor wood structures such as decks and playground equipment were treated with chromated copper arsenic and leaches into the soil and onto the walking surfaces). It is noted that arsenic in the soil tested from two of every five back yards exceeded EPA's Superfund cleanup level of 20 ppm.

Up to 90% of most people's lives are spent indoors where they are exposed to indoor pollutants. See, e.g., Centers for Disease Control and Prevention and U.S. Department of Housing and Urban Development. Healthy housing reference manual. Atlanta: US Department of Health and Human Services; 2006, the contents of which are incorporated herein by reference in their entireties.

The Root Cause—Disrupted Epigenetics

The most recent Global Burden of Disease Study reported that air pollution is responsible for 19% of the overall cardiovascular mortality, including 23% of all deaths from ischemic heart disease and 21% of those from stroke. Epigenetic mechanisms are thought to have a central role not only as relevant elements of the pathogenic mechanism, but also as mediators of the body adaptation to environmental stimuli, such as air pollutants. Alterations in epigenetic marks have also been associated with human diseases including cancer, cardiovascular, respiratory and neurodegenerative disorders. The most investigated epigenetic mechanism is DNA methylation, which implies the adding of cytosine residues located in the CG dinucleotide. See. e.g., Ferrari, L., Carugno, M. & Bollati, V. Particulate matter exposure shapes DNA methylation through the lifespan. *Clin Epigenet* 11, 129 (2019). https://doi.org/10.1186/s13148-019-0726-x, the contents of which are hereby incorporated by reference in their entirety.

Validation of PM 2.5's Disruptive Epigenetics

In a study, 48 healthy male workers were recruited who were free of cardiovascular heart disease from the Boilermaker Union Local 29, located in Quincy, Massachusetts over six sampling cycles between January 2007 to June 2012. The study showed that PM can penetrate into the blood stream directly or can cause an immune response in the lung and, in turn, increase the risk of (cardiovascular disease) CVD development. Heart rate variability (HRV), which is the measurement of variation in the time interval between heartbeats, has been investigated extensively as a prognostic marker of various forms of CVD. Changes in HRV as a reflection of cardiac autonomic function have been suggested as pathophysiological mechanisms or pathways linking CVD mortality and air pollution exposure. A Dust-Trak Aerosol Monitor was used to measure ambient PM 2.5 from a tube, secured to the participant's shoulder and placed in the nasal breathing area during the welding shift to measure PM 2.5 exposure (both) during welding and the absence of welding. Each participant was continuously measured for (EEG) heart activity using a Holter monitor. Blood (samples) from (correlated) time points were drawn in the morning (and) afternoon. The association between PM exposure and mtDNA (mitochondria) methylation and between mtDNA methylation intensities and HRV outcomes were examined. Also examined was the effect of modification by mtDNA methylation in the PM-HRV relationship by including an interaction term between mtDNA methylation levels and PM exposure. To test all associations, linear mixed-effects regression models with random intercepts were performed for each participant to account for multiple measures. The interactions between PM 2.5 and mtDNA methylation were significantly and positively associated with the measured HRV markers. Participants with higher mtDNA methylation levels were more susceptible to the effect of PM 2.5 on HRV measures. See, e.g., https://doi.org/10.1161/JAHA.116.003218, the contents of which are hereby incorporated by reference in their entirety.

Venerest Therapy

The development of Venerest Epigenetic Therapy began with the intent of finding a 100%, plant-based, GRAS therapeutic composition for lung disease, especially lung cancer. The COVID-19 pandemic emergency stimulated a reformulation to deal with the anti-inflammatory and anti-viral aspects of the disease. Upon closer examination, it became clear that, while a therapeutic which might favorably modulate or eliminate COVID-19 symptoms and might have great value to easing the challenges of health care professionals and patients associated with its peak outbreaks, the original formula could be configured to go much further and aim to resolve the irreversible, long term exacerbating health issues associated with PM 2.5 invasions.

The Venerest is a therapeutic inhalant utilizing seven plant derived components, the use of each backed by published studies archived in the National Center for Biotechnical Information as evidence based alternative medicine. Provided herein is a detailed description of novel chemical "scaffolding" between the components without creating a new molecule and which through this innovation provides (to varying degrees): anti-viral, anti-inflammatory, anti-tumor, anti-mutagenic, anti-hyperlipidemic, anti-allergic, anti-oxidant properties; and improved cognitive neuroplasticity.

Anecdotal results from otherwise healthy persons, many who were COVID-19 symptomatic, trend to validating that were the Venerest inhaled by one-half of a study group such as is depicted by the 48 healthy workers in the Study set forth above, it would be expected that clear evidence of Venerest use would have protected the lungs of 24 of those workers from the epigenetic disruption caused by the PM 2.5.

Venerest was in vivo evaluated for short term upper airway toxicity, and demonstrated that it was non-toxic.

Venerest is recommended for use with as an aerosol canister for use in a metered dosage inhaler (MDI) or; as liquid that may refill an approved nebulizer. A sixty (60) day supply, packaged as a 2 oz. bottle, would provide three (3) doses per day.

Aldehyde Functional Monoterpenoids

Monoterpenoids consist of a 10 carbon backbone (2 isoprene units) structure and can be divided into three subgroups: acyclic, monocyclic, and bicyclic. Within each group, the monoterpenoids may be simple unsaturated hydrocarbons or may have functional groups and be alcohols, aldehydes, and ketones. Common aliphatic examples include myrcene, citral, geraniol, lavandulol, and linalool. Representatives of monocyclic monoterpenoids include α-terpineol, limonene, thymol, menthol, carvone, eucalyptol, and perillaldehyde. The bicyclic monoterpenes may be divided into three classes according to the size of the second ring. The first being a six-membered ring in each class while the second can be either a three, four, or five-membered ring. Thujone and $\Delta^3$-carene are representatives of the group containing 6+3-membered rings, α- and β-pinene represent a 6+4 group, while borneol and camphor, a 6+5 group.

Compositions are provided comprising a combination of one or more aldehyde functional monoterpenoids, e.g., three aldehyde functional monoterpenoids including neral, geranial, and citronellal.

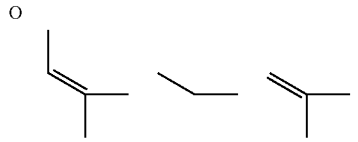

neral

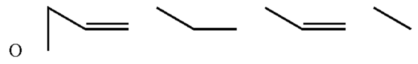

Geranial

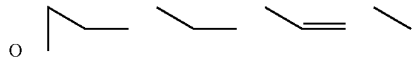

Citronellal

Flavones

Flavones are a class of flavonoids based on the backbone of 2-phenylchromen-4-one (2-phenyl-1-benzopyran-4-one). Flavones are common in the food supply, mainly from spices, and red—purple fruits and vegetables. Common flavones include apigenin (4',5,7-trihydroxyflavone), luteolin (3',4',5,7-tetrahydroxyflavone), tangeritin (4',5,6,7,8-pentamethoxyflavone), chrysin (5,7-dihydroxyflavone), and 6-hydroxyflavone. Flavones have effects on CYP (P450) activity, which are enzymes that metabolize most drugs in the body.

In addition to the aldehyde functional monoterpenoid, e.g., the combination of three aldehyde functional monoterpenoids (neral, geranial, and citronellal), the composition further comprises a hydroflavone, e.g., the hydroflavone 3,3',4',7-tetrahydroxyflavone.

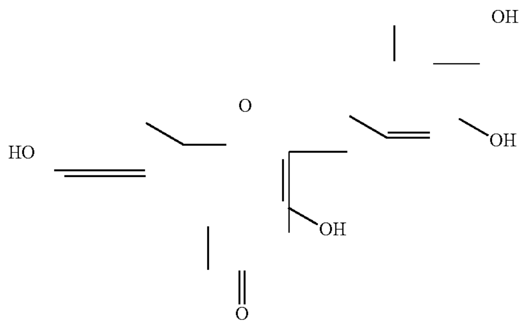

3,3',4,7-Tretahydroxyflavone

Fisetin (3,3',4',7-tetrahydroxyflavone) is found in various fruits and vegetables, such as strawberry, apple, persimmon, grape, onion, and cucumber.

Zinc

An optional component of the formulation is zinc. The mineral zinc has been demonstrated by clinical evidence to block the RNA-dependent RNA polymerase sequence. This results in the reduced production of viral RNA. Zinc must enter the cell to achieve this reduction in viral RNA production. Preparation of the lipid-rich, cell wall for zinc penetration is accomplished when the ionic zinc (+2) is attached to an ionophore. The ligand chemistry of the aldehyde functional monoterpenoids can act as an ionophore. Zinc gluconate in solution is another route to achieve proportionate efficacies. While zinc in association with gluconate or the aldehyde functional monoterpenoid can be employed, zinc associated with other pharmaceutically acceptable counterions can also be employed, such as the pharmaceutically acceptable salts described elsewhere herein.

Ribofuranosyl Picolineamide

In certain embodiments, a ribofuranosyl picolineamide, e.g., a beta-D-ribofuranosylpicolineamide is employed in the treatment method as an optional component. For example, the inclusion of a plant derived, 5-beta-D-ribofuranosylpicolineamide adenine-dinucleotide molecule has added: 1) up-regulated, ambient redox potential for the aldehyde functional, monoterpenoid via protein docking and binding to the virus spines, 2) enhanced phyto-flavonoid solubility via additional grafting and 3) greater anti-inflammatory influence. The plant-based components as employed in the treatment method can be obtained from plant material through the use of a sub-critical butane extraction solvent. The qualities of non-toxic residue, recoverable, high yield and relatively low initial cost may offer advantages to preparing compositions for use in the embodiments. None of the conventional plant extraction methods including the use of solvents such as methanol, ethanol, DMSO as well as cold-pressing and steam distillation yielded extracts with high purity COA.

Viral Infections

The compositions of the embodiments are efficacious in treating infections of the respiratory system.

A lung infection can be caused by a virus, bacteria, or a fungus. One of the most common types of lung infections is pneumonia. Pneumonia, which affects the smaller air sacs of the lungs, is most often caused by contagious bacteria, but can also be caused by a virus. A person becomes infected by breathing in the bacteria or virus after a nearby infected person sneezes or coughs. When the large bronchial tubes that carry air to and from the lungs become infected, it is referred to as bronchitis. Bronchitis is more likely to be caused by a virus than by bacteria. Viruses can also attack the lungs or the air passages that lead to the lungs. This is called bronchiolitis. Viral bronchiolitis most commonly occurs in infants.

Lung infections like pneumonia are usually mild, but they can be serious, especially for people with weakened immune systems or chronic conditions, such as chronic obstructive pulmonary disease (COPD), or comorbidities such as lung based, small cell carcinoma or mesothelioma.

The most common microorganisms responsible for bronchitis include viruses such as the influenza virus or respiratory syncytial virus (RSV), and coronaviruses, bacteria such as *Mycoplasma pneumoniae, Chlamydia pneumoniae, Bordetella pertussis, Streptococcus pneumonia, Haemophilus influenzae,* and *Mycoplasma pneumoniae.* Lung infections can be caused by fungi such as *Pneumocystis jirovecii, Aspergillus,* or *Histoplasma capsulatum.* A fungal lung infection is more common in people who are immunosuppressed, either from certain types of cancer or HIV or from taking immunosuppressive medications.

Examples include coronaviruses that can cause pulmonary effects include the common cold, SARS-associated coronavirus (SARS-CoV, SARS-CoV-2), MERS-associated corona virus (MERS-CoV), COVID-19, influenza viruses such as Influenza A (H1N1) virus, Zika virus (a member of the virus family Flaviviridae), and Marburg virus. Of particular concern are the pulmonary effects of COVID-19, especially in older adults and those who have serious chronic medical conditions such as heart disease, diabetes, or lung disease. Symptoms of COVID-19 infection include fever, cough, and shortness of breath. In adults, emergency warning signs include difficulty breathing or shortness of breath, persistent pain or pressure in the chest, new confusion or inability to arouse, and bluish lips or face.

There are currently no medications specifically approved for COVID-19. About 80% of people with mild COVID-19 illness will recover on their own by drinking plenty of fluids, resting, and taking pain and fever medications. However, some people may become seriously ill and can develop difficulty breathing. However, some patients develop pneumonia and require medical care or hospitalization.

Definitions

The following abbreviations are used herein:

| Abbreviation | Definition |
|---|---|
| % | Percent |
| Abs | Absorbance |
| ° C. | Degrees Celsius |
| µL | Microliter(s) |
| CoA | Certificate of Analysis |
| Conc. | Concentration |
| CV | Coefficient of variation |
| % CV | Percent coefficient of variation (precision) |
| DPBS | Dulbecco's Phosphate-Buffered Saline |
| G | Gram(s) |

-continued

| Abbreviation | Definition |
|---|---|
| GLP | Good Laboratory Practice |
| HCl | Hydrochloride |
| Hr | Hour(s) |
| ID | Identification |
| LDH | Lactate dehydrogenase |
| Mg | milligram |
| mL | Milliliter(s) |
| Ohm | (Ω) Ohm |
| MTT | (3-[4,5-dimethylthiazol-2-yl]-2,5-diphenyltetrazolium bromide; thiazolyl blue) |
| N/A | Not applicable |
| Ng | Nanogram |
| No. or # | Number |
| OD | Optical Density |
| OECD | Organization for Economic Co-operation and Development |
| PC | Positive Control |
| QC | Quality control sample(s) |
| RT | Room temperature |
| SD | Standard deviation |
| Sec | Seconds |
| TA | Test article |
| TEER | Transepithelial Electrical Resistance |
| VC | Vehicle Control |

The term "alcohol" as used herein is a broad term, and is to be given its ordinary and customary meaning to a person of ordinary skill in the art (and is not to be limited to a special or customized meaning), and refers without limitation to any compound as described herein incorporating one or more hydroxy groups, or being substituted by or functionalized to include one or more hydroxy groups.

The term "derivative" as used herein is a broad term, and is to be given its ordinary and customary meaning to a person of ordinary skill in the art (and is not to be limited to a special or customized meaning), and refers without limitation to any compound as described herein incorporating one or more derivative groups, or being substituted by or functionalized to include one or more derivative groups. Derivatives include but are not limited to esters, amides, anhydrides, acid halides, thioesters, and phosphates.

The term "hydrocarbon" as used herein is a broad term, and is to be given its ordinary and customary meaning to a person of ordinary skill in the art (and is not to be limited to a special or customized meaning), and refers without limitation to any moiety comprising only carbon and hydrogen atoms. A functionalized or substituted hydrocarbon moiety has one or more substituents as described elsewhere herein.

The term "lipid" as used herein is a broad term, and is to be given its ordinary and customary meaning to a person of ordinary skill in the art (and is not to be limited to a special or customized meaning), and refers without limitation to saturated and unsaturated oils and waxes, derivatives, amides, glycerides, fatty acids, fatty alcohols, sterol and sterol derivatives, tocopherols, carotenoids, among others.

The terms "pharmaceutically acceptable" as used herein is a broad term, and is to be given its ordinary and customary meaning to a person of ordinary skill in the art (and is not to be limited to a special or customized meaning), and refers without limitation to those compounds, materials, compositions, and/or dosage forms which are, within the scope of sound medical judgment, suitable for contact with the tissues of and/or for consumption by human beings and animals without excessive toxicity, irritation, allergic response, or other problem complications commensurate with a reasonable risk/benefit ratio.

The terms "pharmaceutically acceptable salts" and "a pharmaceutically acceptable salt thereof" as used herein are broad terms, and are to be given their ordinary and customary meaning to a person of ordinary skill in the art (and is not to be limited to a special or customized meaning), and refer without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity. In addition to salts, pharmaceutically acceptable precursors and derivatives of the compounds can be employed. Pharmaceutically acceptable amides, lower alkyl derivatives, and protected derivatives can also be suitable for use in compositions and methods of preferred embodiments. While it may be possible to administer the compounds of the preferred embodiments in the form of pharmaceutically acceptable salts, it is generally preferred to administer the compounds in neutral form.

The term "pharmaceutical composition" as used herein is a broad term, and is to be given its ordinary and customary meaning to a person of ordinary skill in the art (and is not to be limited to a special or customized meaning), and refers without limitation to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids or bases. Pharmaceutical compositions will generally be tailored to the specific intended route of administration.

As used herein, a "carrier" as used herein is a broad term, and is to be given its ordinary and customary meaning to a person of ordinary skill in the art (and is not to be limited to a special or customized meaning), and refers without limitation to a compound that facilitates the incorporation of a compound into cells or tissues. For example, without limitation, dimethyl sulfoxide (DMSO) is a commonly utilized carrier that facilitates the uptake of many organic compounds into cells or tissues of a subject. Water, saline solution, ethanol, and mineral oil are also carriers employed in certain pharmaceutical compositions.

As used herein, a "diluent" as used herein is a broad term, and is to be given its ordinary and customary meaning to a person of ordinary skill in the art (and is not to be limited to a special or customized meaning), and refers without limitation to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood. When a tincture or other liquid form is prepared, animal, vegetable oils, or mineral oils suitable for human consumption can advantageously be employed as diluents. For example, suitable vegetable oils include but are not limited to olive oil, coconut oil, MCT (mixed chain triglycerides derived from coconut oil), and avocado oil.

As used herein, an "excipient" as used herein is a broad term, and is to be given its ordinary and customary meaning to a person of ordinary skill in the art (and is not to be limited to a special or customized meaning), and refers without limitation to a substance that is added to a pharmaceutical composition to provide, without limitation, bulk, consistency, stability, binding ability, lubrication, disintegrating ability etc., to the composition. A "diluent" is a type of excipient.

As used herein, a "subject" as used herein is a broad term, and is to be given its ordinary and customary meaning to a person of ordinary skill in the art (and is not to be limited to a special or customized meaning), and refers without limitation to an animal that is the object of treatment, observation or experiment. "Animal" includes cold- and warm-blooded vertebrates and invertebrates such as fish, shellfish, reptiles, and, in particular, mammals. "Mammal" includes, without limitation, dolphins, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "treating," "treatment," "therapeutic," or "therapy" are broad terms, and are to be given their ordinary and customary meaning (and are not to be limited to a special or customized meaning) and, without limitation, do not necessarily mean total cure or abolition of the disease or condition. Any alleviation of any undesired markers, signs or symptoms of a disease or condition, to any extent, can be considered treatment and/or therapy. Furthermore, treatment may include acts that may worsen the patient's overall feeling of well-being or appearance.

The terms "therapeutically effective amount" and "effective amount" as used herein are broad terms, and are to be given its ordinary and customary meaning to a person of ordinary skill in the art (and are not to be limited to a special or customized meaning), and are used without limitation to indicate an amount of an active compound, or pharmaceutical agent, that elicits the biological or medicinal response indicated. For example, a therapeutically effective amount of compound can be the amount needed to prevent, alleviate or ameliorate markers or symptoms of a condition or prolong the survival of the subject being treated. This response may occur in a tissue, system, animal or human and includes alleviation of the signs or symptoms of the disease being treated. Determination of a therapeutically effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

The term "solvents" as used herein is a broad term, and is to be given its ordinary and customary meaning to a person of ordinary skill in the art (and is not to be limited to a special or customized meaning), and refers without limitation to compounds with some characteristics of solvency for other compounds or means, that can be polar or nonpolar, linear or branched, cyclic or aliphatic, aromatic, naphthenic and that includes but is not limited to: alcohols, derivatives, diesters, ketones, acetates, terpenes, sulfoxides, glycols, paraffins, hydrocarbons, anhydrides, heterocyclics, among others.

Pharmaceutical Compositions

Compositions including the three aldehyde functional monoterpenoids (neral, geranial, and citronellal) in combination with 3,3',4',7-tetrahydroxyflavone, zinc, and a 5-beta-D-ribofuranosylpicolineamide adenine-dinucleotide molecule are provided, optionally with least one excipient (e.g., a sterile combination of vegetable glycerin and water as a carrier fluid). When made bio-available, numerous clinical studies support the efficacy of the terpenoids and flavonoids with anti-viral and antiangiogenic properties respectively. Zinc has also demonstrated anti-viral activity. The flavonoid 3,3',4',7-tetrahydroxyflavone has shown promising results as a senescent but is known to be relatively insoluble, making it difficult to present in vivo. However, as a low energy graft at carbonyl sites located on the terpenoid ligand(s), the compounded molecules easily disperse and remain in suspension as nanometer sized clusters (10-50 nm) through an emulsification process, e.g., using vegetable glycerin as a dissolving surfactant. Accordingly, while the monoterpenoids, zinc, flavonoid, and ribofuranosyl picolineamide molecule can be administered in a simple admixture, it is generally preferred to administer them with the flavonoid in a complex with one or more of the monoterpenoids and one or more of the monoterpenoids as an ionophore for zinc (or, alternatively, with the zinc provided as zinc gluconate). It is also generally preferred to administer the compositions through inhalation (e.g., as a vapor, a mist, or an aerosol), other routes of administration are also contemplated. Delivery devices include inhalers, humidifiers, and the like.

The components of the composition are readily available through conventional sources, and the compositions can offer immediate help to those infected, e.g., with a virus such as COVID-19 or other coronaviruses, especially those with severe lung congestion that cannot find a hospital bed with ventilator support.

The compositions described herein can be administered by themselves to a subject, or in compositions where they are mixed with other active agents, as in combination therapy, or with carriers, diluents, excipients or combinations thereof. Formulation is dependent upon the route of administration chosen. Techniques for formulation and administration of the compounds described herein are known to those skilled in the art (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

The compositions disclosed herein may be manufactured by a process that is itself known, e.g., by means of conventional mixing, dissolving, emulsifying, or extracting processes. Many of the compounds used in the pharmaceutical combinations disclosed herein may be provided as salts with pharmaceutically acceptable counterions.

Multiple techniques of administering pharmaceutical compositions exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Contemplated herein are any methods suitable for administering the composition to a portion of the respiratory system (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

In practice, the three aldehyde functional monoterpenoids (neral, geranial, and citronellal) in combination with ionic zinc, 3,3',4',7-tetrahydroxyflavone, and 5-beta-D-ribofuranosylpicolineamide adenine-dinucleotide molecule may be combined as active ingredient(s) in intimate admixture with a pharmaceutical carrier according to conventional pharmaceutical compounding techniques. The carrier can take a wide variety of forms depending on the form of preparation desired for administration. Thus, the compositions provided herein can be presented as discrete units suitable for pulmonary administration such as vials containing a predetermined amount of the active ingredients. Further, the compositions can be presented as an aqueous or nonaqueous solution, as an emulsion, or on or in a carrier as employed for providing a pharmaceutical composition to the lungs. In addition to the common dosage forms set out above, the compounds provided herein, or pharmaceutically acceptable salts or derivatives thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both.

The compositions can be provided via a humidifier (e.g., an ultrasonic, mist, or vaporizer humidifier) as are commonly available over-the-counter. Other devices for administering include inhalers. The most common type of inhaler is the pressurized metered-dose inhaler (MDI) which is made up of 3 standard components—a metal canister, plastic actuator, and a metering valve. In MDIs, medication is typically stored in solution in a pressurized canister that contains a propellant, although it may also be a suspension. The MDI canister is attached to a plastic, hand-operated actuator. On activation, the metered-dose inhaler releases a fixed dose of medication in aerosol form. The correct procedure for using an MDI is to first fully exhale, place the mouth-piece of the device into the mouth, and having just started to inhale at a moderate rate, depress the canister to release the medicine. The aerosolized medication is drawn into the lungs by continuing to inhale deeply before holding the breath for 10 seconds to allow the aerosol to settle onto the walls of the bronchitis and other airways of the lung. Dry powder inhalers (DPI) release a metered or device-measured close of powdered medication that is inhaled through a DPI device. Nebulizers supply the medication as an aerosol created from an aqueous formulation. Nasal inhalers deliver drugs to the upper respiratory tract. Propellants for inhalers include hydrofluoroalkane (HFA).

The pharmaceutical compositions may contain the three aldehyde functional monoterpenoids (neral, geranial, and citronellal) in combination with ionic zinc, 3,3',4',7-tetrahydroxyflavone, and 5-beta-D-ribofuranosylpicolineamide adenine-dinucleotide molecule in an amount effective for the desired therapeutic effect. In some embodiments, the compositions are provided in a carrier (e.g., glycerin and water) at a concentration of 0.1% to 10% by weight for each of the six components. Depending upon the mode of delivery, higher or lower concentrations may be employed. The composition can be provided in a unit dosage form and comprise from about 0.1 mg or less to about 5000 mg or more of each of the six active ingredients per unit dosage form. Such dosage forms may be provided in a ready to use form, or can be reconstituted in a suitable carrier fluid for delivery via aerosol, mist, vapor, or the like for inhalation administration.

Compositions provided herein can be prepared as solutions or suspensions of the active compound(s) in water or oil or other liquid carrier. A suitable surfactant can be included such as, for example, hydroxypropylcellulose. Dispersions can also be prepared in glycerol, liquid polyethylene glycols, and mixtures thereof in oils. Further, a preservative can be included to, for example, prevent the detrimental growth of microorganisms.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Compositions containing a compound provided herein, or pharmaceutically acceptable salt or derivative thereof, can also be prepared in powder or liquid concentrate form for dilution.

The three aldehyde functional monoterpenoids (neral, geranial, and citronellal), ionic zinc, 3,3',4',7-tetrahydroxyflavone, and 5-beta-D-ribofuranosylpicolineamide adenine-dinucleotide molecule may be present in a single formulation or in multiple formulations provided together, or may be unformulated. In some embodiments, the three aldehyde functional monoterpenoids (neral, geranial, and citronellal), ionic zinc, 3,3',4',7-tetrahydroxyflavone, and 5-beta-D-ribofuranosylpicolineamide adenine-dinucleotide molecule can be administered with one or more additional agents together in a single composition. For example, the monoterpenoids can be administered in one composition, the flavone can be administered in a second composition, the zinc in ionic form in a third composition, and the 5-beta-D-ribofuranosylpicolineamide adenine-dinucleotide molecule in a fourth composition. In a further embodiment, the three aldehyde functional monoterpenoids (neral, geranial, and citronellal), ionic zinc, 3,3',4',7-tetrahydroxyflavone, and 5-beta-D-ribofuranosylpicolineamide adenine-dinucleotide molecule are co-packaged in a kit. For example, a drug manufacturer, a drug reseller, a physician, a compounding shop, or a pharmacist can provide a kit comprising three aldehyde functional monoterpenoids (neral, geranial, and citronellal), ionic zinc, 3,3',4',7-tetrahydroxyflavone, and 5-beta-D-ribofuranosylpicolineamide adenine-dinucleotide molecule for delivery to a patient.

Some embodiments described herein relate to a composition, which can include a therapeutically effective amount of three aldehyde functional monoterpenoids (neral, geranial, and citronellal), ionic zinc, 3,3',4',7-tetrahydroxyflavone, and 5-beta-D-ribofuranosylpicolineamide adenine-dinucleotide molecule. The pharmaceutical composition can include each of the monoterpenoids in, for example, >0.001%, ≥0.01%, ≥1%, ≥2%, ≥3%, ≥4%, ≥5%, ≥6%, ≥7%, ≥8%, ≥9%, ≥10%, ≥20%, or more of the composition. In some embodiments, the pharmaceutical composition can include the flavone in, for example, >0.001%, ≥0.01%, ≥1%, ≥2%, ≥3%, ≥4%, ≥5%, ≥6%, ≥7%, ≥8%, ≥9%, ≥10%, ≥20%, or more of the composition. In some embodiments, the pharmaceutical composition can include the ionic zinc in, for example, >0.001%, ≥0.01%, ≥1%, ≥2%, ≥3%, ≥4%, ≥5%, ≥6%, ≥7%, ≥8%, ≥9%, ≥10%, ≥20%, or more of the composition. In some embodiments, the pharmaceutical composition can include the 5-beta-D-ribofuranosylpicolineamide adenine-dinucleotide molecule in, for example, >0.001%, ≥0.01%, ≥1%, ≥2%, ≥3%, ≥4%, ≥5%, ≥6%, ≥7%, ≥8%, ≥9%, ≥10%, ≥20%, or more of the composition. The pharmaceutical composition can include each of the monoterpenoids in, for example, 0.1% or less to 10% or more, for example, 0.1% to 10%, or 0.5% to 5% or 1% to 3% of the composition. In some embodiments, the pharmaceutical composition can include the flavone in, for example, 0.1% or less to 10% or more, for example, 0.1% to 10%, or 0.5% to 5% or 1% to 3% of the composition. In some embodiments, the pharmaceutical composition can include the ionic zinc in, for example, 0.1% or less to 10% or more, for example, 0.1% to 10%, or 0.5% to 5% or 1% to 3% of the composition. In some embodiments, the pharmaceutical composition can include the 5-beta-D-ribofuranosylpicolineamide adenine-dinucleotide molecule in, for example, 0.1% or less to 10% or more, for example, 0.1% to 10%, or 0.5% to 5% or 1% to 3% of the composition.

Ingestible and Non-Ingestible Compositions

Some embodiments described herein relate to a composition, which can include an effective amount of component(s) (e.g., the three aldehyde functional monoterpenoids (neral, geranial, and citronellal), ionic zinc, 3,3',4',7-tetrahydroxyflavone, and 5-beta-D-ribofuranosylpicolineamide adenine-dinucleotide molecule). In addition to pharmaceutical compositions, also contemplated are ingestible and non-ingestible compositions such as dietary supplements, foodstuffs, and similar composition are also contemplated. Foodstuffs and other comestibles including the compositions disclosed herein are provided, wherein the foodstuff has been fortified (e.g., enriched or concentrated) or additized with one or more components as described herein (e.g., one or more of the aldehyde functional monoterpenoids (e.g., neral, geranial, and citronellal), ionic zinc, 3,3',4',7-tetrahydroxyflavone, and 5-beta-D-ribofuranosylpicolineamide adenine-dinucleotide molecule). The component(s) may be added to foodstuffs for consumption by a subject. The component(s) may be integrated into one or more ingredients of a foodstuff. The component(s) may be prepared as an ingredient, or may be unprepared. The compound, or preparation including the compound, may be added prior to preparation, during preparation, or following preparation. Preparation may without limitation include cooking, mixing, flavoring, seasoning, blending, boiling, frying, baking, or other processes known in the art. Fortification is preferably at a level so as to provide a therapeutic or an effective dosage of the component(s) as described elsewhere herein; however, beneficial effects may also be obtained at amounts below such dosages.

The component(s) may be present as a constituent in foodstuffs by operation of processes known in nature, for example, by altering the metabolic processes of a plant, animal, bacteria, or fungus. Genetic alteration of a plant, animal, bacteria, or fungus to increase the concentration of the component(s) is contemplated. By way of example, the component(s) can be present in the foodstuff in a concentration of at least about 0.01%, at least about 0.1%, at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, or higher, for example, 1% to 2% or 3% or 4% or 5% or 6% or 7% or 8% or 9% or 10% or 20% or 30% or 40% or 50%, e.g., from about 0.01% to about 50%, e.g., from about 0.1% to about 20%, e.g., from about 1% to about 15%, e.g., from about 1% to about 10% e.g., from about 1% to about 5%.

As used herein, an "ingestible composition" includes any composition that, either alone or together with another substance, is suitable to be taken by mouth whether intended for consumption or not. The ingestible composition includes both "food or beverage products" and "non-edible products". By "Food or beverage products", it is meant any edible product intended for consumption by humans or animals, including solids, semi-solids, or liquids (e.g., beverages) and includes functional food products (e.g., any fresh or processed food claimed to have a health-promoting and/or disease-preventing properties beyond the basic nutritional function of supplying nutrients) as well as dietary supplements in a unit dosage form. The terms "non-food or beverage products" or "noncomestible composition" or "noningestible composition" includes any product or composition that can be taken into the mouth by humans or animals for purposes other than consumption or as food or beverage. For example, the non-food or beverage product or noncomestible composition can include supplements, nutraceuticals, pharmaceutical, natural products, over the counter medications, or, e.g., the component(s) as described herein, for delivery to a human or other animal, using a delivery device such as, e.g., oral care products such as dentifrices and mouthwashes, and chewing gum.

The component(s) can be used in the manufacture of chewing gum, lozenges, candies, mints, powders or liquids suitable for reconstitution into a beverage or for addition to a foodstuff, sublingual tablets or lozenges adapted to dissolve when placed under the tongue, capsules, or the like.

Indications

Provided herein are compositions and methods for treating pulmonary infections, e.g., viral pulmonary infections such as COVID-19. These conditions are treated by administration of a 3,3',4',7-tetrahydroxyflavone, optionally in combination with a combination of aldehyde functional monoterpenoids (e.g., the three monoterpenoids neral, geranial, and citronellal), optionally in combination with ionic zinc, and optionally in combination with a 5-beta-D-ribofuranosylpicolineamide adenine-dinucleotide molecule in a suitable carrier.

As is readily apparent to one skilled in the art, the useful in vivo dosage to be administered and the particular mode of administration will vary depending upon the age, weight, the severity of the condition, and mammalian species treated, the particular forms of the components employed, and the specific use for which these components are employed. The determination of effective dosage levels, that is the dosage levels necessary to achieve the desired result, can be accomplished by one skilled in the art using routine methods, for example, in vivo studies. Reference may be made to, for example, "Estimating the Maximum Safe Starting Dose in Initial Clinical Trials for Therapeutics in Adult Healthy Volunteers," U.S. Food and Drug Administration, July 2005.

In some embodiments, a method provided herein may comprise administering a therapeutically effective amount of a composition provided herein.

The dosage may vary broadly, depending upon the desired effects and the therapeutic indication. Alternatively, dosages may be based and calculated upon the surface area or weight of the patient, as understood by those of skill in the art. The exact dosage is determined on a case-by-case basis, or, in some cases, is left to the informed discretion of the subject. The daily dosage regimen for an adult human patient may be, for example, a dose of each of the monoterpenoids, the ionic zinc, the flavone, or the ribofuranosyl picolineamide of from about 0.01 mg to about 10000 mg, from about 1 mg to about 5000 mg, from about 5 mg to about 2000 mg, from about 10 mg to about 1000 mg, or from about 50 mg to about 500 mg. A single dose may include each of the monoterpenoids, the ionic zinc, the flavone, or the ribofuranosyl picolineamide in about 0.01 mg, about 0.1 mg, about 1 mg, about 5 mg, about 10 mg, about 20 mg, about 50 mg, about 100 mg, about 200 mg, about 300 mg, about 400 mg, about 500 mg, about 600 mg, about 800 mg, about 900 mg, about 1000 mg, about 2000 mg, about 5000 mg, or more. The dosage may be adjusted according to the body mass of the subject, for example, the dosage may be about 0.001 mg/kg, about 0.01 mg/kg, about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 15 mg/kg, about 20 mg/kg, about 25 mg/kg, about 30 mg/kg, or higher of each of the monoterpenoids, the ionic zinc, the flavone, or the ribofuranosyl picolineamide.

The dosage may be a single one or a series of two or more given in the course of one or more days, as is appropriate for the individual subject. In some embodiments, the composition is administered until symptoms subside, or for a period of continuous therapy, for example for about one day, two days, three days or more, or a week or more (e.g., one week, two weeks, three weeks, or more). In some embodiments, the combination can be administered or inhaled one time per day, two times per day, three times per day, or more, or continuously.

As is understood by those of skill in the art, in certain situations it may be necessary to administer the compounds disclosed herein in amounts that exceed the above-stated, preferred dosage range in order to effectively treat a subject.

Unit dosage forms can also be provided, e.g., individual vials with a premeasured amount of the composition, configured for administration on a predetermined schedule. Unit dosage forms configured for administration one to three times a day are preferred; however, in certain embodiments it is desirable to configure the unit dosage form for administration more than three times a day, or less than one time per day, or for continuous administration.

Dosage amount and interval are adjusted to the individual subject to provide plasma levels of the active moiety which are sufficient to maintain predetermined parameters, indicators, or marker values, or minimal effective concentration (MEC). Dosages necessary to achieve the desired result will depend on individual characteristics and route of administration. However, assays, for example, HPLC assays or bioassays, may be used to determine serum concentrations.

While the compositions of the embodiments can be useful for treating pulmonary symptoms (e.g., cough, shortness of breath, headaches), pulmonary conditions (e.g., COPD, emphysema), or infections such as lung infections (e.g., coronavirus infections such as COVID-19), the compositions are also useful in supporting cognitive function, wellbeing, mood, and focused thinking. The compositions are useful in imparting optimism and positive energy. The mood improving or enhancing properties can be useful for individuals suffering from a medical condition that may impact mood, e.g., infection, lung disease, cognitive impairment (e.g., Alzheimer's disease or neurodegenerative disease), or other acute or chronic diseases.

EXAMPLE 1

A patient infected with COVID-19 and exhibiting pulmonary symptoms is administered as a sterile mixture a composition comprising three aldehyde functional monoterpenoids (neral, geranial, and citronellal) and 3,3',4',7-tetrahydroxyflavone in vegetable glycerin and water. The composition is delivered to the patient by inhalation, the composition being diffused into a mist with a sonic impulse at 130 Hz. The gentle, cool, tiny mist droplets are inhaled deep into the lungs with minimal irritation and with noticeable, substantially immediate results in the relief of constricted breathing and of cold and flu-like symptoms.

EXAMPLE 2

When zinc was added to the waterborne formula as described in Example 1, then inhaled through a nebulizer by a symptomatic individual, anecdotal evidence showed immediate (less than 15 minutes) reduction in coughing with improved airway comfort and substantial gains in breathing capacity during the following two hour period.

EXAMPLE 3

A patient infected with COVID-19 and exhibiting pulmonary symptoms is administered as a sterile mixture a composition comprising three aldehyde functional monoterpenoids (neral, geranial, and citronellal), 3,3',4',7-tetrahydroxyflavone and a 5-beta-D-ribofuranosylpicolineamide adenine-dinucleotide molecule in vegetable glycerin and water. The composition is delivered to the patient by inhalation, the composition being diffused into a mist with a sonic impulse at 130 Hz. The gentle, cool, tiny mist droplets are inhaled deep into the lungs with minimal irritation and with noticeable, substantially immediate results in the relief of constricted breathing and of cold and flu-like symptoms.

EXAMPLE 4

A patient infected with COVID-19 and exhibiting pulmonary symptoms is administered as a sterile mixture a composition comprising three aldehyde functional monoterpenoids (neral, geranial, and citronellal), 3,3',4',7-tetrahydroxyflavone, zinc in ionic form, and a 5-beta-D-ribofuranosylpicolineamide adenine-dinucleotide molecule in vegetable glycerin and water. The composition is delivered to the patient by inhalation, the composition being diffused into a mist with a sonic impulse at 130 Hz. The gentle, cool, tiny mist droplets are inhaled deep into the lungs with minimal irritation and with noticeable, substantially immediate results in the relief of constricted breathing and of cold and flu-like symptoms.

EXAMPLE 5

The purpose of the study was to evaluate the effects of Venerest on tissue viability, barrier function, and tissue morphology using the EpiAirway™ tissue model. EpiAirway™ (AIR-100), produced by MatTek Corporation, was used to evaluate the potential toxic effects of the test compound Venerest. Control EpiAirway™ tissues were either left untreated (negative control) or treated with 0.5% Triton X-100 as a positive control for cell death. Venerest vapor was applied using a mesh nebulizer. Vapor was applied to the apical surface of the tissues for 5 seconds, based on the manufacturer's recommended in vivo dose of a single 4-second inhale. The tissues were then incubated at 37° C., 5% $CO2$ for 24 hours. Tissue viability was evaluated using the lactate dehydrogenase (LDH) assay. Barrier function was evaluated by transepithelial electrical resistance (TEER) measurement prior to exposure and after the 24-hour recovery period. Tissue morphology was evaluated via hematoxylin-eosin (H&E) staining of tissue sections which were fixed at 24 hours. A 5-second exposure to Venerest vapor using the supplied soft mist sonic mesh nebulizer had no effect on tissue viability, morphology, or barrier function in EpiAirway™ tissues.

The EpiAirway™ model (AIR-100) was a highly differentiated in vitro human airway culture derived from primary human tracheal/bronchial epithelial cells. The human airway epithelial cells have been cultured to form a 3-dimensional (3D) model of human airway epithelial tissue. Morphologically, EpiAirway™ was of uniform thickness and was very similar to native nasal and tracheal epithelial tissue in that it exhibits a pseudostratified morphology and contains both ciliated and mucin producing cells. EpiAirway™ tissues possess in vivo-like barrier properties due to the formation of functional tight junctions between adjacent epithelial cells. These tissues can be utilized to evaluate the effects of topically applied compounds on barrier function, tissue viability, and tissue morphology.

This study evaluated the effects of the test compound Venerest in parallel with positive and negative control treatments. The vaporized test article was applied to the apical surface of the tissues (n=3) for 5 seconds, after which tissues were returned to the incubator for a 24-hour recovery period. TEER of the tissues was measured before exposure and after the 24-hour recovery period (24-hour time point) to determine the effect on barrier function. Following TEER measurement at the 24-hour time point, the tissues were fixed for H&E staining and imaging, and the basal media was collected to determine tissue viability using the LDH assay.

The positive control for cell death was supplied by MatTek Corporation. 0.5% Triton was made by diluting a 1% Triton X-100 stock solution (MatTek #TC-TRI) 1:1 dH2O. A description was maintained in the raw data including lot number, storage conditions, expiration date, and any other relevant information.

Table 1 provides a description of Test Article #1.

TABLE 1

| | |
|---|---|
| Batch/Lot No: | N/A |
| Identity: | Venerest |
| Purity: | N/A |
| Expiration Date: | N/A |
| Storage Condition: | Room Temperature |
| Description: | Liquid |
| Handling Precautions | Follow the SDS for relevant occupational safety information. |
| Supplier: | Sponsor |

Table 2 provides a description of the Positive Control (PC).

TABLE 2

| | |
|---|---|
| Batch/Lot No: | 081419BBA |
| Identity: | 0.5% Triton X-100 in PBS |
| Purity: | N/A |
| Expiration Date: | Aug. 14, 2020 |
| Storage Condition: | Room Temperature |
| Description: | Positive control for cell death |
| Handling Precautions | Relevant occupational safety information was detailed in the MSDS provided by manufacturer |
| Supplier: | MatTek Corporation |

Table 3 provides a description of the carrier for the Positive Control.

TABLE 3

| | |
|---|---|
| Batch/Lot No: | 041520RJ |
| Identity: | dH2O, sterile filtered |
| Purity: | 17.26 MΩ |
| Expiration Date: | Apr. 15, 2021 |
| Storage Condition: | Room Temperature |
| Description: | Liquid |
| Handling Precautions | Relevant occupational safety information was detailed in the MSDS provided by manufacturer |
| Supplier: | MatTek Corporation |

The EpiAirway™ (AIR-100) human tissue model (Lot #32761) produced by MatTek Corporation was used for this study. As part of standard quality control (QC) procedures, random tissues from the tissue lot to be used for the study were measured for transepithelial electrical resistance (TEER) according to MatTek SOPs. The mean TEER value must be ≥300 Ω*cm2 to accept the tissue lot for use. For Lot #32728, the average TEER value was 820.2±91.8 Ω*cm2.

Based on the TEER results obtained from the standardized quality control test, the EpiAirway™ tissues used in this study meet the QC acceptance criteria.

The solvents and reagents employed are described in Table 4.

TABLE 4

| Material | Lot # |
|---|---|
| AIR-100-ASY | 041020AGB |
| TEER-BUFFER | 031020SDC |
| Formalin Lot | 040920SD |
| LDH Kit Lot | AI9P003 |
| 1.0N HCl | 111419GSR |

One positive control for cell death (Triton X-100) was run concurrently with the test article. MatTek Corporation supplied the positive control used for this study.

Documentation of receipt and quality of all assay controls was maintained within the study file. For each treatment group, three wells of 6-well plates were labeled according to Table 5. Each well was filled with 1 mL of pre-warmed EpiAirway™ media (AIR-100-ASY). A dear 96-well plate was labeled for duplicate aliquots of the basal media and one blank media control for LDH analysis at the 24-hour time point. A 12-well plate fitted with a hanging top (MatTek part #HNG-TOP-12) was placed on a stand at a 45-degree angle to be used to expose the EpiAirway™ tissues. The 45-degree angle was the maximum recommended angle for operation of the nebulizer.

Treatment groups (n=3 tissues) are described in Table 5.

TABLE 5

| Group | Test Article | Description |
|---|---|---|
| 1 | NC | Negative Control (Untreated) |
| 2 | PC | Positive Control (0.5% Triton X-100) |
| 3 | TA | Venerest |

The mesh nebulizer (provided by the Sponsor) was fitted with a flexible silicone mouthpiece.

The Venerest solution was mixed thoroughly just prior to filling the reservoir of the nebulizer. 3 mL of the Venerest solution was pipetted into the reservoir. AIR-100 tissues were moved to a 24-well plate containing 250 μL of TEER buffer to rinse the basal side of the insert. The apical surface of the tissues was gently rinsed twice by adding 400 μL of TEER. buffer to the apical surface and carefully aspirating to remove all liquid and mucus from the tissue surface. TEER was measured for each tissue by the following steps:

1. Equilibrate the EVOM2 voltohmmeter:
   a. Fill the Endohm12 culture cup with TEER buffer and turn on the power switch.
   b. Wait at least 20 minutes before measuring TEER.
   c. After equilibration, record the background ohms reading with the culture cup filled with TEER buffer.
   d. Proceed with measuring the TEER.
2. After the tissues have been rinsed, record any macroscopic observations (leakiness, texture, etc.).
3. Add 250 μL of TEER buffer to the apical surface of each tissue.
4. Remove all but ~2 mL of TEER buffer from the culture cup.
5. Using forceps transfer a tissue insert to the culture cup and replace the lid.
6. Measure and record the ohms reading once it has stabilized.
7. Replace the tissue in the rinse plate and continue with the next tissue insert. Repeat until all tissues have been measured.
8. Aspirate the apical TEER buffer after completing the TEER measurement.

Following pre-exposure TEER measurement, the negative and positive control tissues were transferred to the prepared 6-well plates containing media. 100 uL of 0.5% Triton X-100 was applied to the apical surface of the positive control tissues. The tissues of treatment group 3 were transferred to the 12-well plate fitted with a hanging top mounted at a 45-degree angle to allow for use of the nebulizer. The silicone mouthpiece of the nebulizer was fitted over one EpiAirway tissue insert and held sealed against the hanging top. With a seal ensured, the nebulizer was activated and held in place over the EpiAirway tissue for 5 seconds. As the mist was generated, excess mist escaped through the vents of the mouthpiece, indicating a saturated environment within the mouthpiece. This exposure procedure was repeated for the remaining two tissues. After exposure, the tissues were transferred to the prepared 6-well plates containing media and placed into an incubator at 37° C., 5% CO2 for 24 hours.

After 24 hours had elapsed, all tissues were transferred to a new 24-well plate containing 250 μL of TEER buffer to rinse the basolateral surface. The basal media in the 6-well plates was thoroughly mixed and two 25 μL aliquots from each tissue were transferred to a clear 96-well plate and stored at 4° C. for LDH analysis. Tissues were rinsed twice apically with 400 μL TEER buffer to remove any remaining test materials from the apical surface, and TEER was measured by following the steps set forth above. Following the TEER measurement, the tissues were fixed for histological assessment following the procedure as described below.

LDH tissue viability assays were conducted. Basolateral media samples were stored in duplicate 25 μL aliquots (n=3 tissues/group) in a clear 96-well plate. The collected samples were stored at 4° C. wrapped in Parafilm until all time points had been collected. A blank media control was included. To perform the LDH assay, the samples were allowed to warm to room temperature for at least 15 minutes. The required amount of LDH reagent was prepared by mixing Solution A with Solution B at a ratio of 1:45 (A:B). 25 μL of prepared LDH reagent was added to each media sample and incubated at room temperature protected from light for 30 minutes. After 30 minutes, 25 μL of 1 N HCl was added to the wells to stop the LDH reaction. The plate was mixed thoroughly by gently tapping the side of the plate. The absorbance of the samples was read at 490 nm. A background reading at 650 nm was subtracted out.

Histological Analysis was conducted. After the 24-hour TEER measurement, the tissues were moved to a 24-well plate and each well filled with approximately 2 mL 10% formalin to fix the tissues. The tissues were fixed at room temperature overnight. The formalin was removed and replaced with PBS. Using a scalpel, the tissue and insert membrane were removed from the insert and placed in a histology cassette. The samples were dehydrated, paraffin embedded, and sectioned. One slide containing three serial sections of one tissue were stained by H&E and imaged using brightfield microscopy to assess tissue morphology. Data presentation for TEER analysis was conducted as follows.

a. Subtract the background reading from each raw TEER measurement.
b. Multiply this corrected TEER value by the tissue surface area (0.6 cm2 for AIR-100 tissues) to obtain the final TEER value per tissue in Ω*cm2.
c. Calculate the mean and standard deviation from each treatment at each time point (pre-exposure and 24-hours).
d. Determine the percent pre-exposure TEER for the 24-hour time point:

% Pre-Exposure=(TEERFINAL/TEERINITIAL)*100

Where:

TEERFINAL=TEER value at the time point

TEERINTITIAL=TEER value at pre-exposure.

e. Calculate the mean and standard deviation of the percent pre-exposure TEER values for each treatment group at the 24-hour time point.
f. Calculate the mean and standard deviation of the percent untreated negative control (NC) TEER values for each treatment group at the 24-hour time point.

Data presentation for LDH analysis was conducted as follows.

a. Subtract the blank media absorbance from all measurements.
b. Calculate the mean of the technical duplicates to obtain an absorbance for each tissue.
c. Calculate the mean absorbance of the untreated control tissues and the mean of the positive control (Triton x-100 treated) tissues.
d. Determine the percent viability of each tissue:

% Viability=100−[(AbsX−AbsUNT)/(AbsPC−AbsUNT)]*100

Where:

AbsX=absorbance of each tissue sample

AbsUNT=mean absorbance of the untreated tissue group

AbsPC=mean absorbance of the positive control tissue group e. Calculate the mean and standard deviation of the percent viability for each treatment group at the 24-hour time point.

For histological analysis, one representative image of each tissue was presented and observations and interpretations of staining was provided.

Data collection was performed using the SpectraMax Pro software. Data analysis was performed using Microsoft Excel and GraphPad Prism 8. One-way and two-way ANOVA with Tukey's posthoc tests were performed to compare between treatments. A p-value ≤0.05 was considered significant.

Figure 2:
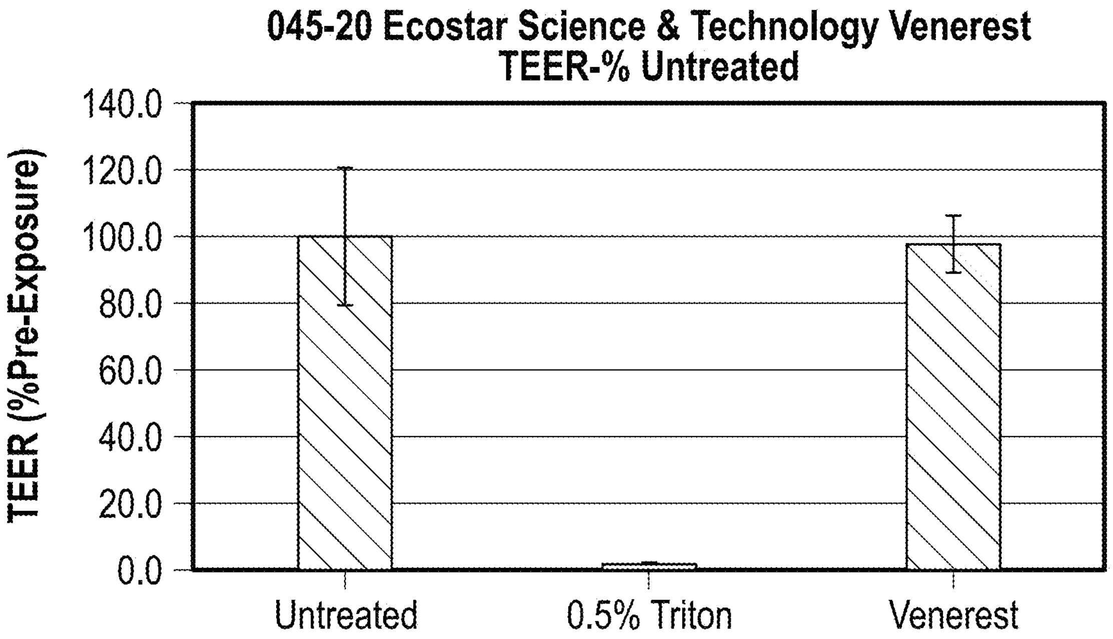
FIG. 2 provides barrier function data for tissue that is untreated, treated with control, or treated with Venerest.

Barrier Function/Transepithelial electrical resistance (TEER) was measured on each tissue before exposure and after the 24-hour recovery period (Raw Data). The TEER of the negative (untreated) control tissues dropped 13.8% during the 24-hour recovery period (637.2±135.2 vs 739.6±37.5 ohms*cm2 pre-exposure FIG. 1, TEER was measured before exposure and after the 24-hour recovery period. Mean and standard deviation are shown for n=3 tissues for each group), but this change was not statistically significant (Statistics). As expected, the TEER of the positive (Triton) control tissues dropped completely during the 24-hour incubation. The TEER of the Venerest treated tissues dropped 16.9% during the 24-hour recovery period (622.8±56.4 vs 749.6±55.9 ohms*cm2 pre-exposure), but this change was also not statistically significant. FIGS. 1 and 2 show the effect of test articles on barrier function.

Figure 3:
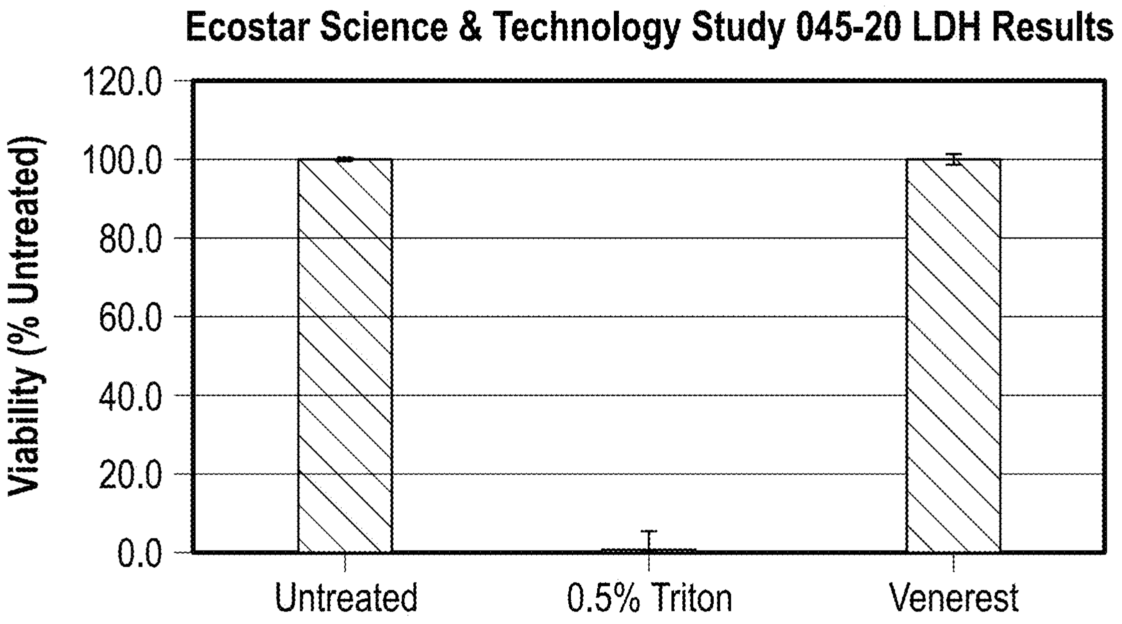
FIG. 3 provides LDH results for tissue that is untreated, treated with control, or treated with Venerest.

Barrier function was also evaluated relative to the untreated control at the 24-hour time point (FIG. 2; TEER was measured before exposure and after the 24-hour recovery period. Results are shown as percent relative to the untreated TEER at the 24-hour time point. Mean and standard deviation are shown for n=3 tissues for each group). In this comparison, the TEER of the Venerest treated tissues was 97.7±8.7% relative to the untreated controls (not significant). Percent viability was calculated relative to the untreated tissues using the LDH assay at the 24-hour time point (FIG. 3; The LDH assay was used to determine the percent viability of each treatment group relative to untreated controls following the 24-hour recovery period. Meaty and standard deviation are shown for n=3 tissues per group). As expected, treatment of the positive control (Triton) tissues resulted in a complete loss of viability. The viability of the Venerest treated tissues was similar to that of untreated controls (100.1±1.0%). FIG. 3 shows percent viability determined by LDH Assay.

The LDH assay was used to determine the percent viability of each treatment group relative to untreated controls following the 24-hour recovery period. Mean and standard deviation are shown for n=3 tissues per group.

Figure 4:
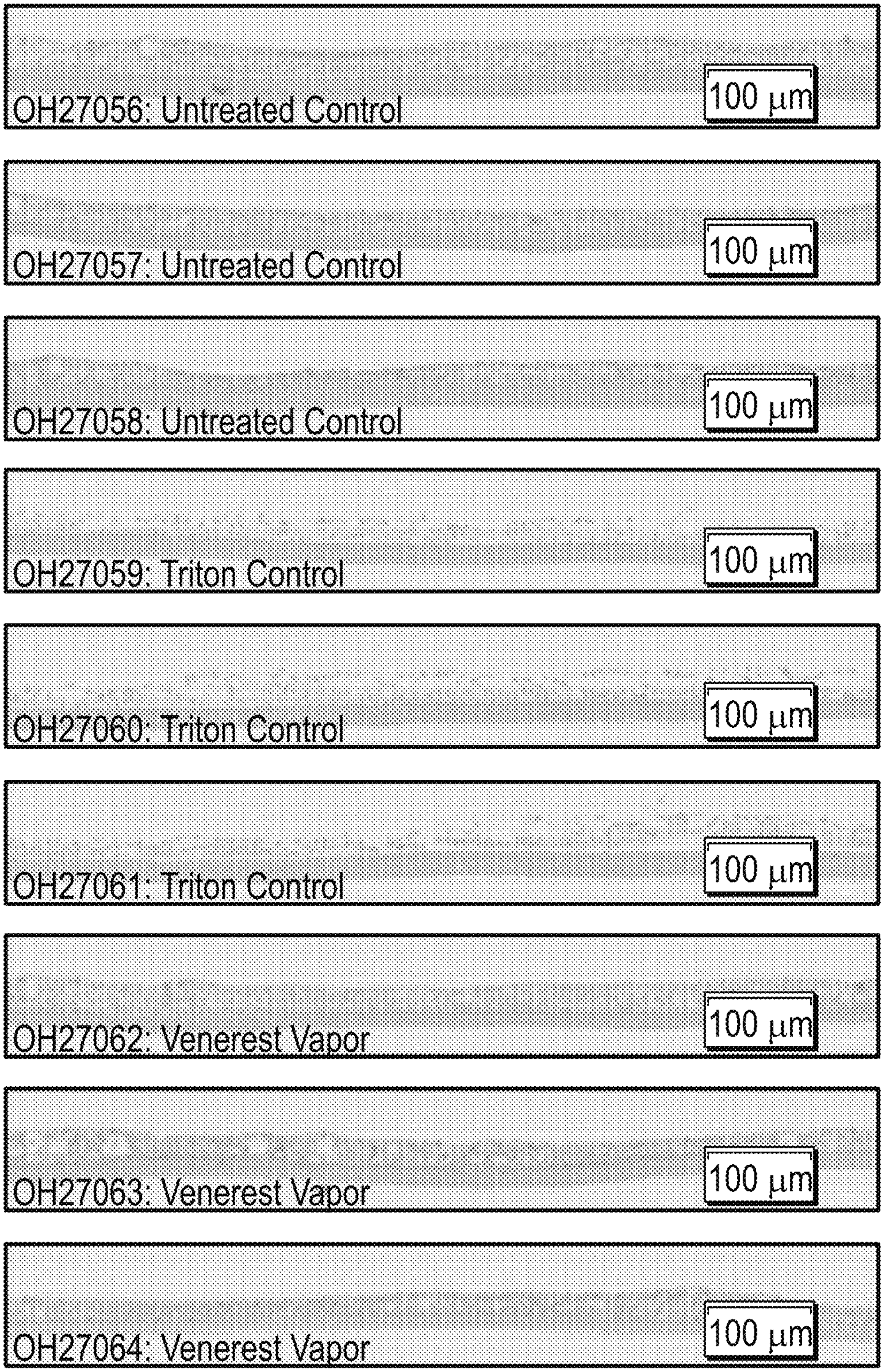
FIG. 4 provides images of tissue that is untreated, treated with control, or treated with Venerest.

Tissue morphology was assessed by H&E staining of all tissues following the 24-hour recovery period. Representative images of each tissue are shown in FIG. 4. The untreated control tissues demonstrated standard EpiAirway™ morphology, with a relatively uniform pseudostratified epithelial morphology and cilia. on the apical surface. As expected, the positive Triton) control tissues showed significant tissue disruption. The Venerest treated tissues showed a similar morphology to untreated control tissues, with a possible slight increase in intracellular vacuoles. FIG. 4 are tissue cross-sections showing the effect of test articles on tissue morphology.

Tissues were fixed at the 24-hour time point, sectioned, and stained by H&E for histological analysis. A representative image from each slide is shown in FIG. 4.

In this study we evaluated the effects of the test compound Venerest on EpiAirway™. The vaporized test article was applied to the apical surface of the tissues (n=3) for 5 seconds, after which tissues were returned to the incubator for a 24-hour recovery period. Transepithelial electrical resistance (TEER) of untreated control tissues did not change significantly during the 24-hour recovery period, indicating an intact barrier. Histological analysis revealed standard EpiAirway™ morphology characteristics, including a pseudostratified morphology and apical cilia. Exposure of tissues to Venerest vapor for 5 seconds using the supplied soft mist sonic mesh nebulizer did not significantly affect TEER, morphology, or tissue viability compared to untreated control tissues, indicating no cytotoxic effects on the EpiAirway™ tissues at the tested dose. Exposure to Venerest in this study was conducted at a single dose, equivalent to two 2-3 second inhalation cycles, based on the manufacturer's recommended use of the product. Future studies may be warranted to examine dosimetry and assess potential toxic effects at higher than recommended doses. EpiAirway™ tissues are a valuable in vitro tool for evaluating the effects of aerosol products on human respiratory epithelial tissues at the air-liquid interface.

Raw data is provided in Tables 6A and 6B and statistics are provided in Tables 7A and 7B.

TABLE 6A

TEER Results

| Test Article | Dose | Pre-Exposure TEER | Ohms*cm2 | Mean | SD | 24 hr TEER | Ohms*cm2 | Mean | SD |
|---|---|---|---|---|---|---|---|---|---|
| | Background | 5 | | | | 5 | | | |
| NC | Untreated | 1304 | 779.4 | 739.6 | 37.5 | 1246 | 744.6 | 637.2 | 135.2 |
| | | 1180 | 705.0 | | | 814 | 485.4 | | |
| | | 1229 | 734.4 | | | 1141 | 681.6 | | |
| PC | 0.5% Triton | 1125 | 672.0 | 749.8 | 80.5 | 20 | 9.0 | 8.6 | 0.3 |
| | | 1393 | 832.8 | | | 19 | 8.4 | | |
| | | 1246 | 744.6 | | | 19 | 8.4 | | |
| TA | Venerest | 1168 | 697.8 | 749.6 | 55.9 | 941 | 561.6 | 622.8 | 56.4 |
| | | 1353 | 808.8 | | | 1126 | 672.6 | | |
| | | 1242 | 742.2 | | | 1062 | 634.2 | | |

TABLE 6B

| LDH Results | | | | | | | | | | |
|---|---|---|---|---|---|---|---|---|---|---|
| | Well | Tissue | OD | Mean OD | SD | Group Mean | SD | % Viability | Mean | SD |
| Untreated | A1 | 1 | 0.065 | 0.064 | 0.001 | 0.066 | 0.004 | 100.2 | 100.0 | 0.4 |
| | A2 | | 0.063 | | | | | | | |
| | A3 | 2 | 0.068 | 0.071 | 0.004 | | | 99.6 | | |
| | A4 | | 0.073 | | | | | | | |
| | A5 | 3 | 0.064 | 0.064 | 0.001 | | | 100.2 | | |
| | A6 | | 0.063 | | | | | | | |
| 0.5% Triton | B1 | 1 | 1.195 | 1.181 | 0.020 | 1.125 | 0.060 | −5.3 | 0.0 | 5.7 |
| | B2 | | 1.167 | | | | | | | |
| | B3 | 2 | 1.064 | 1.062 | 0.004 | | | 6.0 | | |
| | B4 | | 1.059 | | | | | | | |
| | B5 | 3 | 1.132 | 1.132 | 0.000 | | | −0.7 | | |
| | B6 | | 1.132 | | | | | | | |
| Venerest | C1 | 1 | 0.075 | 0.072 | 0.004 | 0.065 | 0.010 | 99.4 | 100.1 | 1.0 |
| | C2 | | 0.069 | | | | | | | |
| | C3 | 2 | 0.053 | 0.053 | 0.000 | | | 101.2 | | |
| | C4 | | 0.053 | | | | | | | |
| | C5 | 3 | 0.068 | 0.069 | 0.001 | | | 99.8 | | |
| | C6 | | 0.069 | | | | | | | |

TABLE 7A

| TEER Statistics-Relevant Comparisons | |
|---|---|
| Compare cell means regardless of rows and columns | |
| Number of families | 1 |
| Number of comparisons per family | 28 |
| Alpha | 0.05 |

| Tukey's multiple comparisons test | Mean Diff. | 95.00% CI of diff. | Significant? | Summary | Adjusted P Value |
|---|---|---|---|---|---|
| Pre exposure: Untreated Control vs. Post 24 hr recovery: Untreated Control | 102.4 | −194.5 to 399.3 | No | ns | 0.9223 |
| Pre exposure: Triton Control vs. Post 24 hr recovery: Triton Control | 741.2 | 444.3 to 1038 | Yes | **** | <0.0001 |
| Pre exposure: Venerest Vapor vs. Post 24 hr recovery: Venerest Vapor | 126.8 | −170.1 to 423.7 | No | ns | 0.8076 |
| Post 24 hr recovery: Untreated Control vs. Post 24 hr recovery: Triton Control | 628.6 | 331.7 to 925.5 | Yes | **** | <0.0001 |
| Post 24 hr recovery: Untreated Control vs. Post 24 hr recovery: Venerest Vapor | 14.4 | −282.5 to 311.3 | No | ns | >0.9999 |
| Post 24 hr recovery: Triton Control vs. Post 24 hr recovery: Venerest Vapor | −614.2 | −911.1 to −317.3 | Yes | **** | <0.0001 |

| Test details | Mean 1 | Mean 2 | Mean Diff. | SE of diff. | N1 | N2 | q | DF |
|---|---|---|---|---|---|---|---|---|
| Pre exposure: Untreated Control vs. Post 24 hr recovery: Untreated Control | 739.6 | 637.2 | 102.4 | 85.75 | 3 | 3 | 1.689 | 16 |
| Pre exposure: Triton Control vs. Post 24 hr recovery: Triton Control | 749.8 | 8.6 | 741.2 | 85.75 | 3 | 3 | 12.22 | 16 |
| Pre exposure: Venerest Vapor vs. Post 24 hr recovery: Venerest Vapor | 749.6 | 622.8 | 126.8 | 85.75 | 3 | 3 | 2.091 | 16 |
| Post 24 hr recovery: Untreated Control vs. Post 24 hr recovery: Triton Control | 637.2 | 8.6 | 628.6 | 85.75 | 3 | 3 | 10.37 | 16 |
| Post 24 hr recovery: Untreated Control vs. Post 24 hr recovery: Venerest Vapor | 637.2 | 622.8 | 14.4 | 85.75 | 3 | 3 | 0.2375 | 16 |
| Post 24 hr recovery: Triton Control vs. Post 24 hr recovery: Venerest Vapor | 8.6 | 622.8 | −614.2 | 85.75 | 3 | 3 | 10.13 | 16 |

TABLE 7B

| LDH Statistics-Relevant Comparisons | | | | | | | | |
|---|---|---|---|---|---|---|---|---|
| Number of families | 1 | | | | | | | |
| Number of comparisons per family | 6 | | | | | | | |
| Alpha | 0.05 | | | | | | | |
| Tukey's multiple comparisons test | Mean Diff. | 95.00% CI of diff. | Significant? | Summary | Adjusted P Value | | | |
| Untreated Control vs. Triton Control | 100 | 94.46 to 105.6 | Yes | **** | <0.0001 | A-B | | |
| Untreated Control vs. Venerest Vapor | −0.1333 | −5.690 to 5.423 | No | ns | 0.9999 | A-C | | |
| Triton Control vs. Venerest Vapor | −100.2 | −105.7 to −94.59 | Yes | **** | <0.0001 | B-C | | |
| Test details | Mean 1 | Mean 2 | Mean Diff. | SE of diff. | n1 | n2 | q | DF |
| Untreated Control vs. Triton Control | 100 | −0.01667 | 100 | 1.985 | 6 | 6 | 71.25 | 20 |
| Untreated Control vs. Venerest Vapor | 100 | 100.1 | −0.1333 | 1.985 | 6 | 6 | 0.09498 | 20 |
| Triton Control vs. Venerest Vapor | −0.01667 | 100.1 | −100.2 | 1.985 | 6 | 6 | 71.34 | 20 |

EXAMPLES 6A-6F

A composition comprising active ingredients as described was prepared. This composition, referred to herein as Venerest, was a light tan colored dispersion with a slightly sweet taste. It was 100% plant based, GRAS compound deliverable as a liquid inhalant through a metered dose inhaler (MDI), compressor driven nebulizer, or soft-mist sonic nebulizer mechanisms. All elements were sustainable with reliable supply chains in various countries around the world. The cost of production was modest. Venerest addressed the following five categories pertinent to the novel chemistry as described herein:

1) Five individual molecules distinct to the particular botanical; grafted as ligands into a hybrid, super-floppy (HSF) molecule. The ligands were ionically scaffolded to provide strategic, timed release;
2) Each molecular structure was designed to provide stero-synergism to mitigate specific pulmonary distresses upon and within the epithelial and goblet structure morphology with special attention to enzymatic response functionalized by nuanced exosomic vesicle, RNA-chemokine-cytokine signaling;
3) Bulk positive symptomatic mitigation was in the following categories: anti-inflammatory, anti-hyperlipidemic, anti-viral, anti-tumor angiogenesis, anti-depressant and anti-aging;
4) Improved cognitive function, mental focus, and physical stamina; and
5) Provided effective chelation for many species of insoluble PM 2.5 contaminants.

While the Venerest HSF molecule has significant, active anti-viral functionality in and of itself, the greatest impact of its stero-synergistic, timed release was to provide a positive modulatory effect upon lung surface cell, exosome emissions, such that these extracellular vesicles 'read' viral threats and respond with the full force and potency of the human body's own immune arsenal. This was done by two distinct mechanisms. The first mechanism was removal from lung mucus, by an encapsulating chelation, of a broad spectrum of PM 2.5 contamination. This neutralizing effect of PM 2.5, which otherwise directly influences and negatively effects the biological process which deal with a myriad of pathological conditions, e.g. autoimmune and infectious diseases, cancer progression, obesity and neurodegenerative diseases. The second mechanism relates to the HSF molecule's prolific, accessible hydroxyl groups together with a high protein docking potential functionality that provides: 1) an active, lipid stripping quanta of the fatty outer shell of the virus and 2) a superior 'escort' environment to the abundant exosome biomolecules to correctly interface and cross communicate with a targeted anti-viral attack of the pathogen.

The Venerest formulation was prepared as follows, with active ingredient present at 12-13% by weight in the excipient. While a particular Venerest formula was prepared, it was noted that in other embodiments the ratios of the components may vary depending upon optimal symptom/organ target and desired nebulizer mist-droplet size. The excipients employed were glycerine, water, and fruit alcohol (i.e., ethanol obtained from fermentation of fruit) in admixture. Fisetin (98% active), a polyphenol, was combined with an excipient mixture of glycerine (vegetable derived), water and fruit alcohol by sonication at 18-24 Hz to <300 nm average particle size. To this mixture was added a pre-mixed clear syrup of fenugreek, glycerine, and purified water, and the combined mixture was subjected to high shear/graft. To this combined mixture was added a pre-mixed clear syrup of lemon balm (*Melissa*), glycerine, and pure water (pre-mixed to clear syrup), which was subjected to graft. To this combined mixture was added a combination of curcumin, fruit alcohol, and water which was subjected to low shear mix. To this combined mixture was added a premixed clear syrup of anise star in water. The resulting Venerest contained 12-13% by mass active ingredient. The resulting Venerest was therapeutically administered to patients. The following was the composition of Venerest (all ratios by weight and all percentages by mass): fisetin (98% active powder)—1.8%; glycerin (for mixing with fisetin)—3.6%; fenugreek essential oil/glycerin/water (20:20:60)—12.6%; lemon balm (*Melissa officialnalis*) essential oil/glycerin/water (20:20:60)—12.6%; curcumin (98% active powder) in a form of a tincture of curcumin/fruit alcohol-ethanol/water (10:10:

80)—1.0%; anis star essential oil/glycerin/water (20:20:60)—1%; water—67.4%; Total components 100.00%.

EXAMPLE 6A

A female patient, age 50, presented with a 102° F. fever, deep rattling, persistent dry cough, loss of appetite, and extreme fatigue. After the first three puffs of Venerest therapy, the patient immediately stopped coughing for four hours, followed by deep sleep later in the day. All symptoms but an occasional cough were gone after five days of Venerest therapy.

EXAMPLE 6B

A female patient, age 73, after a return plane trip to California from a New York family gathering, presented with a dry cough, low grade fever of 99-100° F., persistent headache, no appetite, and breathing difficulties which worsened over the next five days. The patient began Venerest therapy at the third day of increased symptoms. The patient's appetite returned in 24 hours, and the headache ceased in two days. By day three of Venerest therapy, the fever was gone and full breathing resumed. The patient made a full recovery. Another family member on the same trip as patient and having similar symptoms was confirmed to be infected with the COVID-19 virus.

EXAMPLE 6C

A male patient, age 56, was a lifelong smoker. The patient progressively cut smoking from three pack a day to six cigarettes per day. Upon commencement of Venerest therapy, lung congestion and early morning coughing of loose mucus subsided, and energy level and attitude significantly improved.

EXAMPLE 6D

A male patient, age 70, with diabetes self-quarantined with low grade fever, persistent headache, loss of appetite, sleeping difficulty, and deepening breathing difficulty. After a week of symptoms, the patient initiated Venerest therapy, and exhibited full recovery within three days. The patient, who exhibited lifelong depression, attributed a lifting of the depression and improved energy level to the Venerest therapy.

EXAMPLE 6E

A male patient, age 43, exhibiting no health issues initiated Venerest Therapy with two puffs in the morning. At the third day, the patient noticed a significant increase in energy, mental clarity, and sense of well-being.

EXAMPLE 6F

A male patient, age 64, was a long-time smoker but stopped several years ago due to chronic cardiovascular disease issues. The patient exhibited progressive, sudden but intermittent pains in the chest, but was unable to secure a diagnosis. The patient commenced using Venerest Therapy when pains began, and observed that a duration of the pain events shortened. After two months of Venerest Therapy, the patient reported that the chest pain events were less severe and nearly gone.

EXAMPLE 6G

A female patient, age 56, who had used a steam vaporizer for years at the start of each day to clear sinus/lung congestion caused by allergens, began using the Venerest Therapy. After the second day, the patient stopped the use of the steam vaporizer in favor of the Venerest Therapy due to better results with the Venerest Therapy than the steam vaporizer.

EXAMPLE 7

A formula for a supplement adapted to enhance rapid uptake from the oral cavity was developed. The formula comprised 60.65% by weight fenugreek essential oil (prepared by a steam extraction process to preserve steroidal sapinogens and saponins), 9.10% by weigh vegetable glycerine, and 30.25% by weight fisetin (dissolved to a <50 nm paste).

A ten mg (10 mg) dose of the formula, provided as a paste or a starch encrusted tab or a thin film, rapidly and fully dissolves into the oral mucosa without staining the tongue or teeth within one minute (1.0 min). Its effects can be detected in the brain within less than three minutes (3 min). A slowly diffuse, warm, pleasant sustained sense of wellness ensues, with an immediate bio-marker of clearer thinking and focus and sharper eyesight. Taken every four hours at this dosage, the formulation will provide a plural-research established, clinically effective deliverable fisetin element which shows significant, cognitive support while mitigating an fMRI verifiable, reduction of the toxic proteins of amyloid and tau plaque present in the diseased brain's neurological structure(s).

The absorption is facilitated by the saponin's bi-functional, surfactant nature. The main mechanism for the absorption of the compound is via passive diffusion into the lipoid membrane. A secondary route is by endocytosis through the oral epithelium whereupon tissue-supplied, enzymatic response to the novel chemistry begins a delayed metabolic pathway.

The primary transmission route is through the facial arteries, and notably the sub-lingual-to-internal carotid artery, which gives immediate blood brain barrier (BBB) transmission to the cerebral hemisphere.

Research suggests this formula has many, significant, non-obvious elements, including the promise of fisetin to effectively treat or ameliorate cardiovascular disease, Alzheimer's disease, and/or dementia.

EXAMPLE 8

Figure 5:
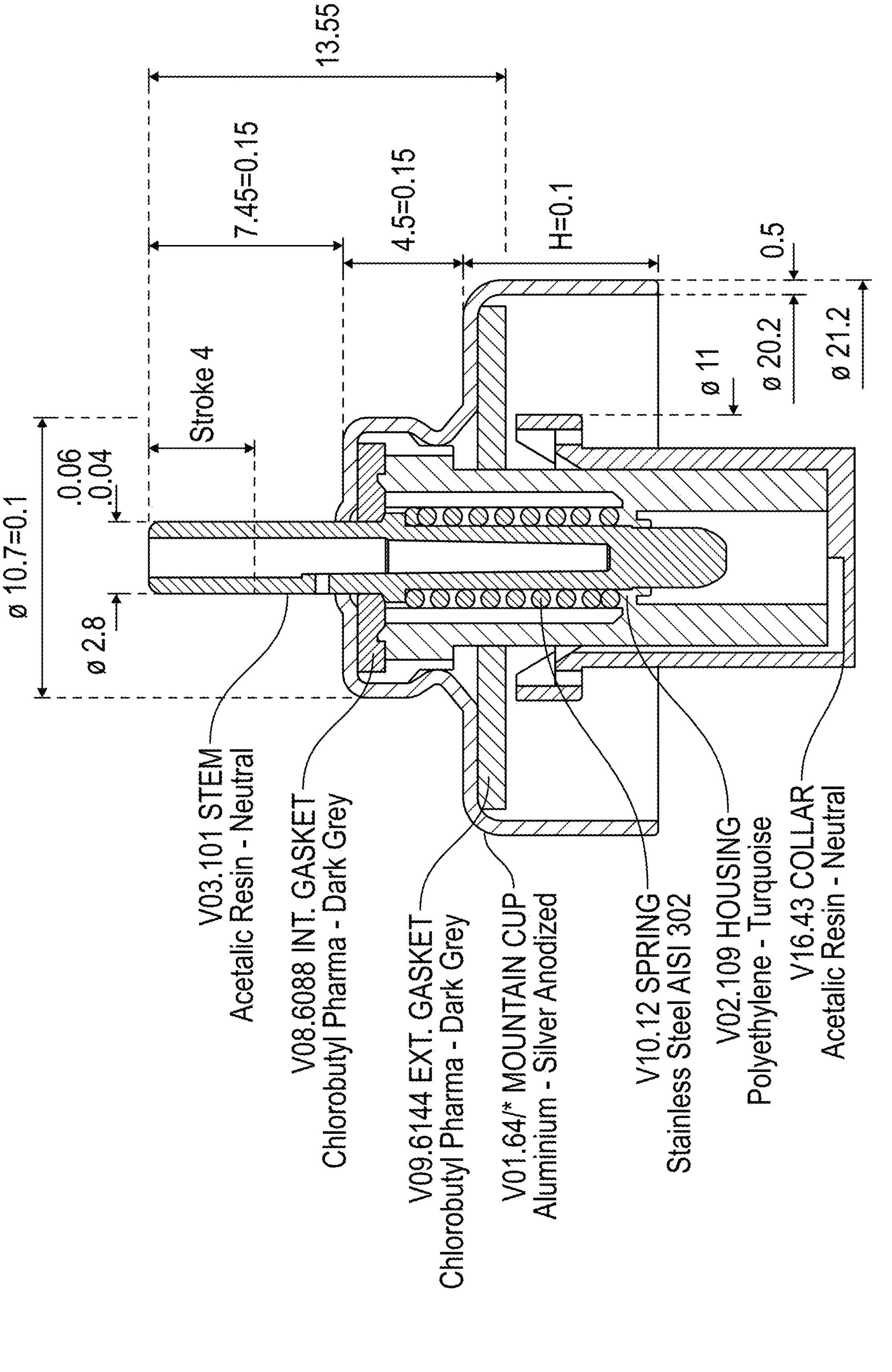
FIG. 5 illustrates an example 100 mcl, 20 mm upside-down metered dose inhaler valve usable for administering any of the various compositions disclosed herein, such as the compositions of Example 8 below.
Figure 6:
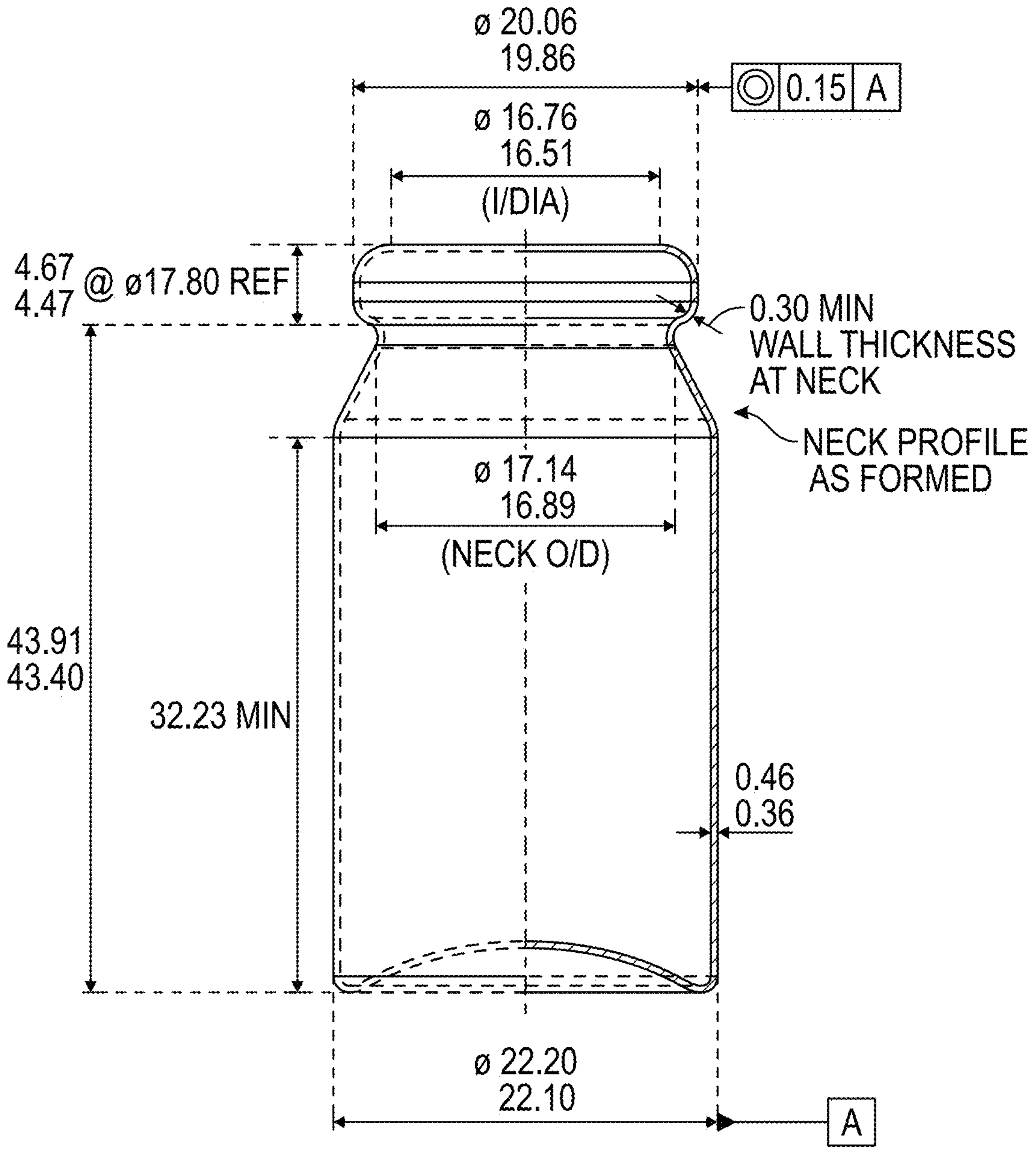
FIG. 6 illustrates an example 14 ml aluminum can comprising an aluminum-magnesium alloy having a 14 ml nominal brimful capacity usable for administering any of the various compositions disclosed herein, such as the compositions of Example 8 below.

Various formulations are prepared for delivery to patients in need thereof, according to the following descriptions of compositions, dosing, and delivery devices in Tables 8A, 8B, 8C, 9, 10, 11, and FIGS. 5 and 6.

TABLE 8A

| VENEREST - Formula No. 1 | | | |
|---|---|---|---|
| 14 mL Canister | 14000 mg | | |
| Valve Size: | 100 mcl | | |
| Venerest Formula | 1.5 g | 1500 mg | 12.82% |
| HFA134a | 10.2 g | 10200 mg | 87.18% |
| Total Ingredients | 11.7 g | 11700 mg | 100.00% |

TABLE 8A-continued

| VENEREST - Formula No. 1 | | | |
|---|---|---|---|
| Doses | 150 ea | 78.00 mg | per dose |
| Venerest Formula | | 10.00 mg | per dose |
| HFA134a | | 68.00 mg | per dose |
| Intake | | 78.00 mg | per dose |

TABLE 8B

| VENEREST - Formula No. 2 | | | |
|---|---|---|---|
| 14 mL Canister | 14000 mg | | |
| Valve Size: | 100 mcl | | |
| Venerest Formula | 1.0 g | 1000 mg | 8.55% |
| R2 Formulation V1 | 0.5 g | 500 mg | 4.27% |
| V1 FORMULATION INCLUDES FDA, GRAS INGREDIENTS (+ETOH) | | | |
| HFA134a | 10.2 g | 10200 mg | 87.18% |
| Total Ingredients | 11.7 g | 11700 mg | 100.00% |
| Doses | 150 ea | 78.00 mg | per dose |
| Venerest Formula | | 6.67 mg | per dose |
| R2 Formulation V1 | | 3.33 mg | per dose |
| HFA134a | | 68.00 mg | per dose |
| | | 78.00 | |

TABLE 8C

| VENEREST - Formula No. 3 | | | |
|---|---|---|---|
| 14 mL Canister | 14000 mg | | |
| Valve Size: | 100 mcl | | |
| Venerest Formula | 1.0 g | 1000 mg | 8.55% |
| R2 Formulation V2 | 0.5 g | 500 mg | 4.27% |
| V2 FORMULATION INCLUDES FDA, GRAS INGREDIENTS (+ETOH) | | | |
| HFA134a | 10.2 g | 10200 mg | 87.18% |
| Total Ingredients | 11.7 g | 11700 mg | 100.00% |
| Doses | 150 ea | 78.00 mg | per dose |
| Venerest Formula | | 6.67 mg | per dose |
| R2 Formulation V2 | | 3.33 mg | per dose |
| HFA134a | | 68.00 mg | per dose |
| | | 78.00 | |

TABLE 9

| Sublingual Formulation | | | | |
|---|---|---|---|---|
| Item No. | Product Description | Weight | M | % Volume |
| 0.01 | Venerest Formula | 1.0 | g | 9.2% |
| 0.02 | MCT (Coconut Oil) | 0.3 | g | 2.8% |
| 0.03 | Magnesium | 0.1 | g | 0.9% |
| 0.04 | L-Theanine | 0.1 | g | 0.9% |
| 0.05 | Cinnamon Bark Extract | 0.1 | g | 0.9% |
| 0.06 | Cinnamon Spirits | 0.025 | g | 0.2% |
| 0.07 | Cinnamon Spirits | 0.025 | g | 0.2% |
| 0.08 | Total Formulation | 1.7 | g | 15.1% |
| | HFA 134a Per Canister | 9.25 | g | 84.9% |
| | Total Weight | 10.9 | g | 100% |
| 0.09 | Total Actuations (+/−10%) | 170 | ea | |
| 0.10 | Dose Per Actuation | 64.12 | mg | |
| 0.11 | Venerest Dose Per Actuation | 5.88 | mg | |
| 0.12 | Other Ingredients | 3.85 | mg | |

TABLE 10

| R2 Components Used | | | |
|---|---|---|---|
| Component No. | Description | Start Weight | |
| 0.01 | 14 mL Aluminum Plasma Coated Canister | 3.82 | g |
| 0.02 | 100 mcl Metered Dose Valve | 2.74 | g |
| | Total Components | 6.56 | g |
| | Total Product Formulation | 1.5 | g |
| | Finished Product | 8.06 | g |

TABLE 11

| Venerest HFA134a/QC - Filing Volumes | | | | | | |
|---|---|---|---|---|---|---|
| COE Unit No. | MONROE Venerest V1 | | R2 V1 | | Tolerances R2 V2 | |
| 0.01 | 10.32 | g | 10.18 | g | 10.39 | g |
| 0.02 | 10.26 | g | 10.37 | g | 10.24 | g |
| 0.03 | 10.27 | g | 10.24 | g | 10.41 | g |
| 0.04 | 10.25 | g | 10.31 | g | 10.49 | g |
| 0.05 | 10.39 | g | 10.37 | g | 10.42 | g |
| 0.06 | 10.22 | g | 10.42 | g | 10.48 | g |
| 0.07 | 10.23 | g | | | | |
| 0.08 | 10.12 | g | | | | |

The example 14 ml canister and 100 mcl metering valve referenced in Example 8 are illustrated in FIGS. 5 and 6. It will be understood that any other suitable administration devices may equally be implemented with any of the compositions disclosed herein, without departing from the spirit or scope of the present technology.

The above description presents the best mode contemplated for carrying out the present technology, and of the manner and process of making and using it, in such full, clear, concise, and exact terms as to enable any person skilled in the art to which it pertains to make and use this present technology. This present technology is, however, susceptible to modifications and alternate constructions from that discussed above that are fully equivalent. Consequently, this technology is not limited to the particular embodiments disclosed. On the contrary, this technology covers all modifications and alternate constructions coming within the spirit and scope of the present technology as generally expressed by the following claims, which particularly point out and distinctly claim the subject matter of the present technology. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the present technology, but instead as merely intended to highlight alternative or additional features that may or may not be utilized in a particular embodiment of the present technology. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is further understood by those within the art that if a specific number of an introduced claim recitation is intended, such an intent is explicitly recited in the claim, and in the absence of such recitation no such intent is present. For example, as an aid to understanding, the following appended claims may contain usage of the introductory phrases 'at least one' and "one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It is further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' is understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Any percentages, ratios or other quantities referred to herein are on a weight basis, unless otherwise indicated.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the present technology to the specific embodiments and examples described herein, but rather to also cover all modification and alternatives coming with the true scope and spirit of the present technology.

What is claimed is:

1. A pharmaceutical product in a form selected from a group consisting of a chewing gum, a lozenge, a sublingual dissolving tablet, a sublingual dissolving paste, an aerosol, and combinations thereof, the pharmaceutical product comprising:

a pharmaceutical composition comprising:

30.25% by weight fisetin;

9.10% by weight glycerin; and 60.65% by weight of fenugreek essential oil .

2. The pharmaceutical product of claim 1, wherein the pharmaceutical product is in a form of a chewing gum.

3. The pharmaceutical product of claim 1, wherein the pharmaceutical product is in a form of a lozenge.

4. The pharmaceutical product of claim 1, wherein the pharmaceutical product is in a form of a sublingual dissolving tablet or paste.

* * * * *